(12) United States Patent  
Paulino

(10) Patent No.: US 9,293,061 B2  
(45) Date of Patent: Mar. 22, 2016

(54) METHOD FOR CREATING A MNEMONIC EXPERIENCE

(71) Applicant: Mecubed, LLC, Miami, FL (US)

(72) Inventor: Anabelle K. Paulino, Miami, FL (US)

(73) Assignee: MECUBED, LLC, Miami, FL (US)

( * ) Notice: Subject to any disclaimer, the term of this patent is extended or adjusted under 35 U.S.C. 154(b) by 0 days.

(21) Appl. No.: 13/757,795

(22) Filed: Feb. 2, 2013

(65) Prior Publication Data

US 2014/0141403 A1   May 22, 2014

Related U.S. Application Data

(60) Provisional application No. 61/595,020, filed on Feb. 3, 2012.

(51) Int. Cl.
*G09B 25/00*    (2006.01)
*G09B 19/00*    (2006.01)

(52) U.S. Cl.
CPC ........................... *G09B 19/00* (2013.01)

(58) Field of Classification Search
CPC ............................................. G09B 1/00
USPC .......................................... 434/236, 238, 365
See application file for complete search history.

(56) References Cited

PUBLICATIONS

Foer, Joshua. Moonwalking with Einstein. New York, NY. Penguin Group (USA), Inc., 2011.
Yates, Frances A. The art of Memory. Chicago, IL. The University of Chicago Press, 1966.
Higbee, Kenneth L. Your Memory: How It Works & How to Improve It. New York, NY. Marlowe & Company, 1977.

*Primary Examiner* — Kesha Frisby
(74) *Attorney, Agent, or Firm* — Loren Donald Pearson Assouline & Berlowe, P.A.

(57) ABSTRACT

A mnemonic system provides a method for creating virtual and real places that can be experienced in person or virtually to cause users to remember and retain presented information. When the place is real, the method can be embodied in a curatorial or thematic experience. The method can be used to create tangible items like a book or game that are written according to the method of the invention. The method can be placed on computer readable media. When the method is executed by a computer, a virtual place, such as a palace, is created for a user to virtually experience. A method is taught for collaborative creation of mnemonic experiences. The collaborative co-creation application of the invention works by allowing people to co-create, contribute, information/facts and images into the standardized architecturally created palace (adhering to all the co-creation steps mentioned herein) creating a complete concentration-specific palace.

21 Claims, 34 Drawing Sheets

1. Select a Concentration

2. Information Gathering

3. Research, Read, Annotate and determine importance of information

4. Select material to be remembered and place in set manner

5. Create REALly Imaginary Palace

6. Create a Primary Character

7. Create and communicate with secondary character/s

8. Go through experience (Walk through, journey, travel)

1. Select a Concentration
2. Information Gathering
3. Research, Read, Annotate and determine importance of information
4. Select material to be remembered and place in set manner
5. Create REALly Imaginary Palace
6. Create a Primary Character
7. Create and communicate with secondary character/s
8. Go through experience (Walk through, journey, travel)

|   | *(Mm)* Internal Operations | *(Mm)* External Web Operations |
|---|---|---|
| 1 | Define Discipline and create Palace | |
| 2 | Define Rooms needed by splitting discipline into X sub disciplines (x dependent on # of rooms requested) | |
| 3 | Release Palace 2D for External Web | Palace opened for editing |
| 4 | Animation starts on general elements – Characters, location, positions for images, etc. Script writing begins with introduction and general layout | Users add facts to Palace and rates it. creating hierarchy of information for each Room |
| 5 | MM Approves Facts. Facts are added into script as become approved. | Users add images to Facts creating hierarchy of images |
| 6 | MM Approves Images. Once image is approved, Location in palace is assigned and added into general animation. | Room is locked when all images are approved. |
| 7 | As full rooms are locked, animation is completed for each room with script integration and camera movement. | Palace is locked when all Rooms are approved. |
| 8 | Final rooms are finished and script integrated. Palace final approval and launch. | |

1. Simonides of Ceos (556 – 468 B.C)
    a. Inventor of the Art of Memory
    b. Poet (1$^{st}$ to demand payment for poetry)
2. Plato(429-347 B.C)
    a. Influenced the Renaissance Movement
    b. Philosopher, mathematician, student of Socrates
    c. Founder of the first institution of higher learning in the west
3. Aristotle (384-322 B.C)
    a. Wrote:
        i. De Memoria et Reminiscentia
            1. Albertus and Aquinas reference this work a lot
            2. 5 Sense
    b. Applied Art Of Memory to his Arguments (pg. 31 of AOM)
    c. Concluded "It is impossible even to think without a mental picture"
        i. "For it is possible to put things before our eyes just as those do who invent mnemonics and construct images".
        ii. He believed "memory belonged to the same part of the soul as imagination".
4. Metrodorus of Scepsis (145-70BC)
    a. Greek
        i. Found 360 Places in 12 signs which sun moves (theory)
        ii. Designed system
            1. Brought star into the system
        iii. Writer and Orator
        iv. Cicero and Quintilian referenced his system and him
        v. Perfected Ad Herennium Technique
5. Tullius (Marcus Tullio Cicero)
    a. Credited with being the author of Ad Herennium

FIG. 9A
PRIOR ART

6. Cicero (106 – 43 BC)
   a. Wrote
      i. De Inventione
      ii. De Oratore (55BC)
         1. Thesis: Show the importance of oratory in society and culture.
   b. 1st to tell story of 5 parts of rhetoric
   c. Philosophy- - Platonic
   d. Roman Philosopher, statesman, lawyer, theorist, constitutionalist, orator, republican.
   e. 1st to tell story of Simonides
   f. Became foundation for Medieval Times Art Of Memory Movement
7. Quintilian (CA 35- CA 100)
   a. Wrote Instituto Oratoria (AD 95) (Composed of 12 books)
   b. Head Educator in Rome during his prime
   c. Visualized writing on a Wax tablet
   d. Roman Rhetorician
   e. Believed in hard work and training the memory
   f. Concluded: Art Originated from experience, said palaces could be public buildings, long journeys, going through cities, use places as wax and images as letters.
      i. Rules in Instituto Oratoria
8. Augustine (354-480)
   a. Pagan teacher on rhetoric
   b. Trained on classical mnemonics
   c. Christian
   d. Seeks god in memory (religious goals in Art of Memory application)
   e. Philosopher, theologian
   f. Wrote:
      i. Confessions: speaks of walking up a staircase and entering fields of memory (AOM quoted)
9. Martianus Capella (5th Century)
   a. "Defining the standard formula of academic learning from the Christianized Roman Empire of the fifth century until the Renaissance of the 12th Century".
   b. Roman Pagan Writer
   c. Contribution to Art of Memory: exercise by night: quieter
   d. Recommends Quintilian approach
   e. Presented Art of Memory in romantic and allegorical style – appealing on times up to medieval times

FIG. 9B
PRIOR ART

10. Boncompagno (1165-1240)
    a. Images
        i. Virtue and Vice
        ii. Heaven and Hell
    b. Foreshadows Art of Memory extension through Albertus and Aquinas
    c. Italian Professor of rhetoric
11. Albertus Magnus (1206-1280)
    a. Wrote
        i. Summa Theologiae
        ii. Summa de Bono
        iii. De Anima
    b. Advocates Aristotle
        i. Stresses Aristotle reminiscence, melancholy, temperament, memory.
        ii. states artificial memory belongs to reminiscence
    c. Advocates use of only real places
        i. Best ex. Church
    d. Morally and religiously followed Tullius
    e. Advocate study of Art of Memory
    f. German Dominican Friar
    g. Alchemist and Magician (allegations)
    h. Explains why poetry started

FIG. 9C
PRIOR ART

12. Ramon Lull (1235-1316)
    a. Wrote:
        i. Ars Magna (1305)
        ii. Ars Brevis (1617)
        iii. Libers ad memoriam confirmandam (1308)
    b. Created the Art of Lullism
        i. Attacked current status of Art of Memory when at its peak by developing different system of Art of Memory
        ii. Trinitarian Structure (reflection of the Trinity)
            1. Focused using 3 powers
                a. As Intellectus (art of knowing or finding truth)
                b. As Voluntas (art of training that will towards loving truth)
                c. As Memoria (art of memory for remembering truth)
        iii. Comes out of philosophical tradition (Augustian Platonism – Neoplatonic) (Not classical Tradition)
        iv. No connection in images between emotional and dramatic corporeal simitude's
        v. Religious goal: convert Jews and Muslims to Christianity
        vi. Penned it as alphabet and attached it scientifically
        vii. Using three images – square, circle and triangle (religious and cosmic significance)
        viii. Works with abstractions (ex. Names of the Gods to B and K.) – Like a mystical and cosmological geometry and algebra
        ix. Visual Image of preference: tree
        x. Admits 2 types of memory, natural and artificial, references Ad Herennium leaving out Tullian rules
            1. Only 1 rule – Repetition and Meditation ( Thomas Aquinas- $4^{th}$ rule)
        xi. Man in Renaissance times with $12^{th}$ century mindset
        xii. Contribution to Art Of Memory
            1. Art of investigation, art of finding out truth by asking questions
        xiii. Hermetic Cabalist

FIG. 9D
PRIOR ART

Thomas Aquinas (1225-1274)
    c. Wrote:
        i. De Summae
        ii. Summae Theologica
    d. Student of Albertus Magnus
    e. Advocate study of Art of Memory
    f. Saint, Italian, Dominican Priest, philosopher, theologian
    g. Used Albertus and Tullius as foundations
    h. Believed in natural theology, father of Thomism
    i. Great Memory
    j. Rules:
        i. 1. Ad Herennium – striking and unusual images
        ii. Aristotle – Order importance
        iii. Ad Herennium – places are not to be crowded because weaken memory
        iv. Aristotle – mediation and repetition
        v. Concludes: Memory is "the sensitive part of the soul which takes the images of sense impressions, it therefore belongs to the same part of the soul as imagination..." (pg. 71 Art Of Memory)
        vi. Renaissance Contribution of impresa: attempt to remember a spiritual intention through a similitude.
13. Petrach (1304-1374)
    a. Early Humanist
        i. Considered father of Humanism
        ii. Considered father of Renaissance
    b. Contributions to Art of Memory
        i. Places should be of medium size
    c. No exact book giving rules or advice
    d. Wrote:
        i. Rerum memorandarum libri (Things to be remembered)(1345)
        ii. Influenced by Cicero's De Inventione
        iii. Artificial Memory comes from Prudence
        iv. Incomplete theory on the 4 cardinal virtues
    e. Catholic Ialian Scholar, Poet
    f. Transition Art of Memory from Medieval Times set to Renaissance mindset

FIG. 9E
PRIOR ART

14. Peter of Ravenna (1448-1508)
    a. Wrote:
        i. Phoenix – sive artificiosas memoria (1491)
            1. Most universally known of all memory books
            2. Wrote in vernacular giving advice (popular)
                a. Gives practical advise
    b. Contribution to Art Of Memory
        i. Advocated quiet places like churches be used
        ii. Place can not be larger than a man can reach
    c. Influenced by Quintillian
        i. Confusion because his mnemonics resembles Medieval tradition in Renaissance Times.
15. Johannes Romberch (1480-1532)
    a. Influenced by Peter of Ravenna
        i. Advocates use of real places
        ii. Advocates places must be no larger than man can reach
    b. Develops a Grammar (creates images) that makes up alphabet and numbers
    c. German Dominican
    d. Wrote:
        i. Congestorium Artificiose Memorie (1520)
    e. Learned straight mnemonics, influenced by Petrarch, humanist tendencies
    f. Implementes signs of Zodiac (influence of Metrodonus) and cosmos
16. Cosmas Rosselius (??? -1578)
    a. Italian Dominican Priest
        i. His order frowned talking
        ii. Created a manual alphabet
    b. Similar ideas with Romberch
    c. End of 16th century
    d. Wrote:
        i. Thesaurus Artificiosa Memoriae (1579)
            1. Divided hell into 11 places and paradise surrounded by wall of sparkling gems
    e. Recommends using real places in Art of Memory Technique
17. Erasmus (1466-1536)
    a. Disliked and negative about Art of Memory (against all magical short cuts to memory)
    b. Concluded memory is based on study and order
    c. Dutch Renaissance Humanist

FIG. 9F
PRIOR ART

18. Guilio Gamilo (1480-1544)
    a. Created organized Memory Theatre
        i. Wrote:
            1. L'idea del Theatro
        ii. Patroned by King of France
            1. Theatre meant to be for King's eyes only
            2. Theatre was never completed nor seen
        iii. Memory Theatre (Vitruvian Type)
            1. Description: Made of wood, many images, many little boxes, 7 grades of steps (in reference to Solomon's 7 pillars), divided by 7 gangways representing the 7 planets, each ahs a symbolic meaning represented by the same image on each of its 7 grades. No audience sitting on stage, solitary spectator stands where stage is looking up and around
            2. Design to represent the order of eternal truth and memorize every notion of Cicero
            3. Theatre represents universe expanding from $1^{st}$ cause through stages of creation. $1^{st}$ simple elements from water... 2. Mixture of elements in the cave... 3. Creation of man's men in image of god... 4 union of man's soul and body... 5. Whole world of man's activities... 6. Man's natural activities... 7. Man's arts and sciences, religions and laws.
            4. Effect of Theatre: power to enable spectator to read off one glance by inspecting images the whole contents of the universe. The 'secret; or one of them was the basic planetary images were to be talismans and have a virtue, almost astral power. Ex. He interpreted magic of Egyptian Statues in artistic sense.
        iv. Based on principles of classical Art of Memory
    b. Influenced by Plato view of Art of Memory
        i. Neoplatonic
    c. Renaissance enters moment of occult influences
        i. Hermetic-Cabalist transitions
            1. Pico De La Mirandolla mentions in his Conclusions and Oration on the Dignity of Man
    d. Christian

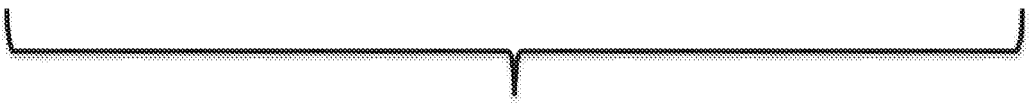

FIG. 9G
PRIOR ART

19. Giordano Bruno (1548-1600)
    a. Wrote:
        i. De Umbris Idearum (1582)
        ii. Most important Series:
            1. Shadows (Paris 1581)
            2. Circes (Paris 1581)
            3. Seals (England 1583)
            4. Statues and Images
                a. Only one of series that did not contain Art of Memory references.
        iii. Last book: Images (1591)(3 parts) (last part 30 seals – which lists various types of occult memory systems- revealing 4 seals – love, art, math and memory).
    b. Italian Friar (Like Camilo – bringing a secret to a King – in this case – King of France – Henry III)
    c. Bruno's System was an inner mystery cult following ancient pattern
        i. Presented as a religious revelation, worried about inner unification on star level
        ii. Contribution to Art of Memory:
            1. All about systemization methods, used allegory within a mnemonic setting
        iii. Approach was from a mind machine angle
    d. Influenced by
        i. Lullism, Peter of Ravenna, Thomas Aquinas and Romberch (for images)
        ii. Main source of magic: Cornelius Agrippa's De Philosophia Occulta
    e. Combined Classical Art of Memory and Lullism by putting classic Art of Memory images in Lullian wheels and adding magic images.
        i. 150 images on Lullian wheel

FIG. 9H
PRIOR ART f. Goal: transmitted Egyptian religious message – extremely magical and religious.
g. Goal: Establish magical ascent within, in the psyche, to result in return of the intellect to unity through organization of significant images ( magical star-images)
h. More daring in use of magical imagery, considered mystical, magical and occult practice
   i. Considered himself as continuing medieval past approach
i. Pre-Greek Egyptian and Hermetic wisdom (anti-Aristotle)
j. Offered a religion (or hermetic experience/inner mystery cult) with 4 guides.
   1. Love (souls raised to divine)
   2. Art (joining the soul to the world)
   3. Mathesis (magical use of figures)
   4. Magic (religious magic)
k. Application of his system: looking for celestial above, 24 rooms in each of 9 memory palaces he created with images.
l. Believed to have founded a sect (Giordanist) which would have been connected to Rosicrucians (Brotherhood behind Rosy Cross)(17$^{th}$ cent)
   i. Influence believed to have reached Rosicrucianism and Freemasonry.
      1. Ex. Occult use of artificial memory in Royal Masonry (Camilo and Bruno)
   ii. Credited with developing Renaissance occult memory in the direction of the secret societies.

FIG. 9I
PRIOR ART

20. Robert Fludd (1574-1637)
    a. Hermetic Cabalist Philosopher (16th Century)
    b. Influenced by Pico de la Mirandolla and Ficino
    c. Renaissance occult tradition
        i. Disciple of Rosicrucians
    d. Contribution to Art of Memory during Renaissance: theatre must be in architectural form
        i. Advocated use of real places
    e. Wrote:
        i. Utiusque Cosmi...technica Historia
            1. Taps the tradition at the time of Rosicrucian fugore
            2. Occult memory system resembling complexity like Bruno
        ii. Declaration (1618)
            1. Defends his and Rosicrucians as harmless followers
    f. Goal: Present his philosophy visually or in hieroglyphics
        i. Images include hieroglyphic engravings
    g. Created a system of squares and circles based on zodiac, occult and magical. It incorporates colors and columns, distinguishes symbols like day and night. There are 10 places, 5 floors, 5 columns in all theatres (which are really stages).
        i. Alleges Ad Herennium and cites it – visually resembles Shakespeare's Global Theatre.
        ii. Speaks of 24 theatres.
        iii. Round Art: image of virtues and vices, like old medieval art
            1. Superior, hard, adapted to Micocosm
            2. Based on round heavens, zodiac and spheres of planets
        iv. Square Art: images of corporeal things, men, animals, inanimate objects, ordinary art of memory (uses Ad Herennium)
            1. Preferred and easier method
            2. Artificial made up places and images
            3. Talismanic or magic images (like Bruno)
        v. Buildings placed in heavens so astrally activated by being organized in relation to the stars

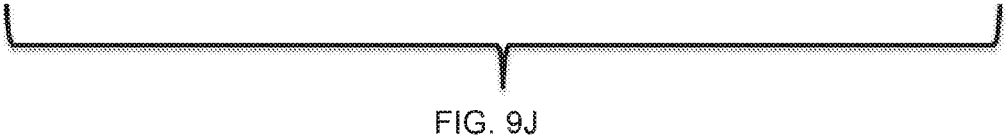

FIG. 9J
PRIOR ART

21. Peter Ramus (1515-1572)
    a. Influenced by Quintillian
    b. Superficial pedagogic method
    c. Many parts reminiscent of Lullism
    d. Rejects locus and imagine rules
        i. Breaks the continuity
    e. Took out memory as part of the rhetoric
        i. Result was abolished artificial memory
    f. Reform and simplification of education through new and better mnemonics
        i. Set each subject in dialectical order
            1. Famous Ramist epitome
    g. Reviving an ancient wisdom "an insight into the nature of reality through which he can unify the multiplicity of appearances"
    h. Repeatedly uses the golden chain image in his system
    i. Socratic pre-Aristotelian (Anti-Aristotle)
22. Campanella (1568-1639)
    a. Wrote:
        i. Citta del Sole
            1. A utopia, ideal city, solar or astral cult, round, with round temple in middle (where all stars of heavens are presented)
    b. Italian Dominican
    c. System: Architecturally like Bruno but simpler with circular walls which hold all the knowledge
        i. Encyclopedic lay-out of a universal memory system
23. Lambert Schenkel (1547-1603)
    a. Student: Johannes Paepp
        i. Reveals the secret of the occult memory hidden in Schenkel's (classical Art of Memory) book
    b. Classical system of Art of Memory
        i. Tries to connect classical with Dominica Religious goals
    c. Wrote
        i. De Memoria (1593)
            1. Valuable source for modern history of Art of Memory
    d. Influenced by Rossellius, Romberch, Aquinas, Bruno

FIG. 9K
PRIOR ART

24. Francis Bacon (1561-1626)
    a. Used Art of Memory
        i. Believed in using active images to impress in memory
        ii. Principles of order and arrangement
    b. Wrote:
        i. Advancement of Learning
            1. Said Memory could be improved, used for practical purposes
    c. Believed Art of Memory used to memorize and later investigate
    d. Wanted to improve inventive logic
25. Rene Descartes (1596-1650)
    a. Wrote
        i. Discours de la method
    b. Had a great memory
    c. More occult than Bacon
        i. Rationalized occult memory
        ii. Lack of interest in imagination
    d. Disliked Lull
    e. Introduced quantitative application of Art of Memory as opposed to qualitative
    f. Goal: to provide universal art or method, based on reality that could be applied for the solution of all problems
        i. Kind of a geometric logic

FIG. 9L
PRIOR ART

26. John Amos Comenius (1592-1670)
    a. Wrote
        i. Orbis Pictus (1658)
            1. Premier for teaching children languages by means of pictures, pictures arranged in order of the world, heavens, stars and celestial phenomenon of animals, birds, stones, etc.
                a. Original Pedagogic methods which made language learning enjoyable
                b. Children learned alphabets in all languages through images on a wall (solarian)
    b. Practical, original and valuable (ex. Learning languages)
27. Gottfried Leibniz (1646-1716)
    a. Created infinitesimal calculus – independent from Isaac Newton
        i. The universal language of system, final goal of Art of Memory
    b. Best example of survival of influences in Art of Memory (from lullism)
        i. Interprets Lullism with arithmetic
    c. Wrote
        i. De Arte Combinatoria
            1. Based on adaptions of Lullism
            2. Very like traditions of classical Art of Memory
        ii. Disputatio de Casibus In Jure (1666)
        iii. Dissertatio de Arte Combinoatira
    d. Goal: inventing a universal calculus using combinations of significant signs or characters
    e. Established notae as joining image of something sensible to the thing to be remembered (using Ad Herennium as basis) (also recalls 3 laws of Aristotelian association)
        i. Established notae as an alphabet (notae as natural as possible) resembles geometric figures like Egyptians and Chinese used before it.
    f. Goal: Message of universal love and brotherhood, religious tolerance, charity and benevolence
    g. Conclusion: Latest Art of Memory influence of current views: using Art of Memory would progress the sciences, lead to extended knowledge of universe, then wider knowledge of God, its creator and then a wider extension of charity, the source of all virtues.
    h. Rosicrucian aura with hermetic traditional marks and Egyptian and Chinese symbols

FIG. 9M
PRIOR ART

1. Simonides of Ceos (556 – 468 B.C)
    a. Inventor of the Art of Memory
    b. Poet (1st to demand payment for poetry)
2. Plato(429-347 B.C)
    a. Influenced the Renaissance Movement
    b. Philosopher, mathematician, student of Socrates
    c. Founder of the first institution of higher learning in the west
3. Aristotle (384-322 B.C)
    a. Wrote:
        i. De Memoria et Reminiscentia
            1. Albertus and Aquinas reference this work a lot
            2. 5 Sense
    b. Applied Art Of Memory to his Arguments (pg. 31 of AOM)
    c. Concluded "It is impossible even to think without a mental picture"
        i. "For it is possible to put things before our eyes just as those do who invent mnemonics and construct images".
        ii. He believed "memory belonged to the same part of the soul as imagination".
4. Metrodorus of Scepsis (145-70BC)
    a. Greek
        i. Found 360 Places in 12 signs which sun moves (theory)
        ii. Designed system
            1. Brought star into the system
        iii. Writer and Orator
        iv. Cicero and Quintilian referenced his system and him
        v. Perfected Ad Herennium Technique
5. Tullius (Marcus Tullio Cicero)
    a. Credited with being the author of Ad Herennium

FIG. 10A
PRIOR ART

6. Cicero (106 – 43 BC)
   a. Wrote
      i. De Inventione
      ii. De Oratore (55BC)
         1. Thesis: Show the importance of oratory in society and culture.
   b. 1st to tell story of 5 parts of rhetoric
   c. Philosophy- - Platonic
   d. Roman Philosopher, statesman, lawyer, theorist, constitutionalist, orator, republican.
   e. 1st to tell story of Simonides
   f. Became foundation for Medieval Times Art Of Memory Movement
7. Quintilian (CA 35- CA 100)
   a. Wrote Instituto Oratoria (AD 95) (Composed of 12 books)
   b. Head Educator in Rome during his prime
   c. Visualized writing on a Wax tablet
   d. Roman Rhetorician
   e. Believed in hard work and training the memory
   f. Concluded: Art Originated from experience, said palaces could be public buildings, long journeys, going through cities, use places as wax and images as letters.
      i. Rules in Instituto Oratoria
8. Augustine (354-480)
   a. Pagan teacher on rhetoric
   b. Trained on classical mnemonics
   c. Christian
   d. Seeks god in memory (religious goals in Art of Memory application)
   e. Philosopher, theologian
   f. Wrote:
      i. Confessions: speaks of walking up a staircase and entering fields of memory (AOM quoted)
9. Martianus Capella (5th Century)
   a. "Defining the standard formula of academic learning from the Christianized Roman Empire of the fifth century until the Renaissance of the 12th Century".
   b. Roman Pagan Writer
   c. Contribution to Art of Memory: exercise by night: quieter
   d. Recommends Quintilian approach
   e. Presented Art of Memory in romantic and allegorical style – appealing on times up to medieval times

FIG. 10B
PRIOR ART

10. Boncompagno (1165-1240)
    a. Images
        i. Virtue and Vice
        ii. Heaven and Hell
    b. Foreshadows Art of Memory extension through Albertus and Aquinas
    c. Italian Professor of rhetoric
11. Albertus Magnus (1206-1280)
    a. Wrote
        i. Summa Theologiae
        ii. Summa de Bono
        iii. De Anima
    b. Advocates Aristotle
        i. Stresses Aristotle reminiscence, melancholy, temperament, memory.
        ii. states artificial memory belongs to reminiscence
    c. Advocates use of only real places
        i. Best ex. Church
    d. Morally and religiously followed Tullius
    e. Advocate study of Art of Memory
    f. German Dominican Friar
    g. Alchemist and Magician (allegations)
    h. Explains why poetry started

FIG. 10C
PRIOR ART

12. Ramon Lull (1235-1316)
    a. Wrote:
        i. Ars Magna (1305)
        ii. Ars Brevis (1617)
        iii. Libers ad memoriam confirmandam (1308)
    b. Created the Art of Lullism
        i. Attacked current status of Art of Memory when at its peak by developing different system of Art of Memory
        ii. Trinitarian Structure (reflection of the Trinity)
            1. Focused using 3 powers
                a. As Intellectus (art of knowing or finding truth)
                b. As Voluntas (art of training that will towards loving truth)
                c. As Memoria (art of memory for remembering truth)
        iii. Comes out of philosophical tradition (Augustian Platonism – Neoplatonic) (Not classical Tradition)
        iv. No connection in images between emotional and dramatic corporeal simitude's
        v. Religious goal: convert Jews and Muslims to Christianity
        vi. Penned it as alphabet and attached it scientifically
        vii. Using three images – square, circle and triangle (religious and cosmic significance)
        viii. Works with abstractions (ex. Names of the Gods to B and K.) – Like a mystical and cosmological geometry and algebra
        ix. Visual Image of preference: tree
        x. Admits 2 types of memory, natural and artificial, references Ad Herennium leaving out Tullian rules
            1. Only 1 rule – Repetition and Meditation ( Thomas Aquinas- $4^{th}$ rule)
        xi. Man in Renaissance times with $12^{th}$ century mindset
        xii. Contribution to Art Of Memory
            1. Art of investigation, art of finding out truth by asking questions
        xiii. Hermetic Cabalist

FIG. 10D
PRIOR ART

Thomas Aquinas (1225-1274)
- c. Wrote:
    - i. De Summae
    - ii. Summae Theologica
- d. Student of Albertus Magnus
- e. Advocate study of Art of Memory
- f. Saint, Italian, Dominican Priest, philosopher, theologian
- g. Used Albertus and Tullius as foundations
- h. Believed in natural theology, father of Thomism
- i. Great Memory
- j. Rules:
    - i. 1. Ad Herennium – striking and unusual images
    - ii. Aristotle – Order importance
    - iii. Ad Herennium – places are not to be crowded because weaken memory
    - iv. Aristotle – mediation and repetition
    - v. Concludes: Memory is "the sensitive part of the soul which takes the images of sense impressions, it therefore belongs to the same part of the soul as imagination…" (pg. 71 Art Of Memory)
    - vi. Renaissance Contribution of impresa: attempt to remember a spiritual intention through a similitude.

13. Petrach (1304-1374)
    - a. Early Humanist
        - i. Considered father of Humanism
        - ii. Considered father of Renaissance
    - b. Contributions to Art of Memory
        - i. Places should be of medium size
    - c. No exact book giving rules or advice
    - d. Wrote:
        - i. Rerum memorandarum libri (Things to be remembered)(1345)
        - ii. Influenced by Cicero's De Inventione
        - iii. Artificial Memory comes from Prudence
        - iv. Incomplete theory on the 4 cardinal virtues
    - e. Catholic Ialian Scholar, Poet
    - f. Transition Art of Memory from Medieval Times set to Renaissance mindset

FIG. 10E
PRIOR ART

14. Peter of Ravenna (1448-1508)
    a. Wrote:
        i. Phoenix – sive artificiosas memoria (1491)
            1. Most universally known of all memory books
            2. Wrote in vernacular giving advice (popular)
                a. Gives practical advise
    b. Contribution to Art Of Memory
        i. Advocated quiet places like churches be used
        ii. Place can not be larger than a man can reach
    c. Influenced by Quintillian
        i. Confusion because his mnemonics resembles Medieval tradition in Renaissance Times.
15. Johannes Romberch (1480-1532)
    a. Influenced by Peter of Ravenna
        i. Advocates use of real places
        ii. Advocates places must be no larger than man can reach
    b. Develops a Grammar (creates images) that makes up alphabet and numbers
    c. German Dominican
    d. Wrote:
        i. Congestorium Artificiose Memorie (1520)
    e. Learned straight mnemonics, influenced by Petrarch, humanist tendencies
    f. Implementes signs of Zodiac (influence of Metrodonus) and cosmos
16. Cosmas Rosselius (??? -1578)
    a. Italian Dominican Priest
        i. His order frowned talking
        ii. Created a manual alphabet
    b. Similar ideas with Romberch
    c. End of 16$^{th}$ century
    d. Wrote:
        i. Thesaurus Artificiosa Memoriae (1579)
            1. Divided hell into 11 places and paradise surrounded by wall of sparkling gems
    e. Recommends using real places in Art of Memory Technique
17. Erasmus (1466-1536)
    a. Disliked and negative about Art of Memory (against all magical short cuts to memory)
    b. Concluded memory is based on study and order
    c. Dutch Renaissance Humanist

FIG. 10F
PRIOR ART

18. Guilio Gamilo (1480-1544)
    a. Created organized Memory Theatre
        i. Wrote:
            1. L'idea del Theatro
        ii. Patroned by King of France
            1. Theatre meant to be for King's eyes only
            2. Theatre was never completed nor seen
        iii. Memory Theatre (Vitruvian Type)
            1. Description: Made of wood, many images, many little boxes, 7 grades of steps (in reference to Solomon's 7 pillars), divided by 7 gangways representing the 7 planets, each ahs a symbolic meaning represented by the same image on each of its 7 grades. No audience sitting on stage, solitary spectator stands where stage is looking up and around
            2. Design to represent the order of eternal truth and memorize every notion of Cicero
            3. Theatre represents universe expanding from $1^{st}$ cause through stages of creation. $1^{st}$ simple elements from water... 2. Mixture of elements in the cave... 3. Creation of man's men in image of god... 4 union of man's soul and body... 5. Whole world of man's activities... 6. Man's natural activities... 7. Man's arts and sciences, religions and laws.
            4. Effect of Theatre: power to enable spectator to read off one glance by inspecting images the whole contents of the universe. The 'secret; or one of them was the basic planetary images were to be talismans and have a virtue, almost astral power. Ex. He interpreted magic of Egyptian Statues in artistic sense.
        iv. Based on principles of classical Art of Memory
    b. Influenced by Plato view of Art of Memory
        i. Neoplatonic
    c. Renaissance enters moment of occult influences
        i. Hermetic-Cabalist transitions
            1. Pico De La Mirandolla mentions in his Conclusions and Oration on the Dignity of Man
    d. Christian

FIG. 10G
PRIOR ART

19. Giordano Bruno (1548-1600)
    a. Wrote:
        i. De Umbris Idearum (1582)
        ii. Most important Series:
            1. Shadows (Paris 1581)
            2. Circes (Paris 1581)
            3. Seals (England 1583)
            4. Statues and Images
                a. Only one of series that did not contain Art of Memory references.
        iii. Last book: Images (1591)(3 parts) (last part 30 seals – which lists various types of occult memory systems- revealing 4 seals – love, art, math and memory).
    b. Italian Friar (Like Camilo – bringing a secret to a King – in this case – King of France – Henry III)
    c. Bruno's System was an inner mystery cult following ancient pattern
        i. Presented as a religious revelation, worried about inner unification on star level
        ii. Contribution to Art of Memory:
            1. All about systemization methods, used allegory within a mnemonic setting
        iii. Approach was from a mind machine angle
    d. Influenced by
        i. Lullism, Peter of Ravenna, Thomas Aquinas and Romberch (for images)
        ii. Main source of magic: Cornelius Agrippa's De Philosophia Occulta
    e. Combined Classical Art of Memory and Lullism by putting classic Art of Memory images in Lullian wheels and adding magic images.
        i. 150 images on Lullian wheel

FIG. 10H
PRIOR ART f. Goal: transmitted Egyptian religious message – extremely magical and religious.
g. Goal: Establish magical ascent within, in the psyche, to result in return of the intellect to unity through organization of significant images ( magical star-images)
h. More daring in use of magical imagery, considered mystical, magical and occult practice
    i. Considered himself as continuing medieval past approach
i. Pre-Greek Egyptian and Hermetic wisdom (anti-Aristotle)
j. Offered a religion (or hermetic experience/inner mystery cult) with 4 guides.
    1. Love (souls raised to divine)
    2. Art (joining the soul to the world)
    3. Mathesis (magical use of figures)
    4. Magic (religious magic)
k. Application of his system: looking for celestial above, 24 rooms in each of 9 memory palaces he created with images.
l. Believed to have founded a sect (Giordanist) which would have been connected to Rosicrucians (Brotherhood behind Rosy Cross)(17$^{th}$ cent)
    i. Influence believed to have reached Rosicrucianism and Freemasonry.
        1. Ex. Occult use of artificial memory in Royal Masonry (Camilo and Bruno)
    ii. Credited with developing Renaissance occult memory in the direction of the secret societies.

FIG. 10I
PRIOR ART

20. Robert Fludd (1574-1637)
    a. Hermetic Cabalist Philosopher (16th Century)
    b. Influenced by Pico de la Mirandolla and Ficino
    c. Renaissance occult tradition
        i. Disciple of Rosicrucians
    d. Contribution to Art of Memory during Renaissance: theatre must be in architectural form
        i. Advocated use of real places
    e. Wrote:
        i. Utiusque Cosmi...technica Historia
            1. Taps the tradition at the time of Rosicrucian fugore
            2. Occult memory system resembling complexity like Bruno
        ii. Declaration (1618)
            1. Defends his and Rosicrucians as harmless followers
    f. Goal: Present his philosophy visually or in hieroglyphics
        i. Images include hieroglyphic engravings
    g. Created a system of squares and circles based on zodiac, occult and magical. It incorporates colors and columns, distinguishes symbols like day and night. There are 10 places, 5 floors, 5 columns in all theatres (which are really stages).
        i. Alleges Ad Herennium and cites it – visually resembles Shakespeare's Global Theatre.
        ii. Speaks of 24 theatres.
        iii. Round Art: image of virtues and vices, like old medieval art
            1. Superior, hard, adapted to Micocosm
            2. Based on round heavens, zodiac and spheres of planets
        iv. Square Art: images of corporeal things, men, animals, inanimate objects, ordinary art of memory (uses Ad Herennium)
            1. Preferred and easier method
            2. Artificial made up places and images
            3. Talismanic or magic images (like Bruno)
        v. Buildings placed in heavens so astrally activated by being organized in relation to the stars

FIG. 10J
PRIOR ART

21. Peter Ramus (1515-1572)
    a. Influenced by Quintillian
    b. Superficial pedagogic method
    c. Many parts reminiscent of Lullism
    d. Rejects locus and imagine rules
        i. Breaks the continuity
    e. Took out memory as part of the rhetoric
        i. Result was abolished artificial memory
    f. Reform and simplification of education through new and better mnemonics
        i. Set each subject in dialectical order
            1. Famous Ramist epitome
    g. Reviving an ancient wisdom "an insight into the nature of reality through which he can unify the multiplicity of appearances"
    h. Repeatedly uses the golden chain image in his system
    i. Socratic pre-Aristotelian (Anti-Aristotle)
22. Campanella (1568-1639)
    a. Wrote:
        i. Citta del Sole
            1. A utopia, ideal city, solar or astral cult, round, with round temple in middle (where all stars of heavens are presented)
    b. Italian Dominican
    c. System: Architecturally like Bruno but simpler with circular walls which hold all the knowledge
        i. Encyclopedic lay-out of a universal memory system
23. Lambert Schenkel (1547-1603)
    a. Student: Johannes Paepp
        i. Reveals the secret of the occult memory hidden in Schenkel's (classical Art of Memory) book
    b. Classical system of Art of Memory
        i. Tries to connect classical with Dominica Religious goals
    c. Wrote
        i. De Memoria (1593)
            1. Valuable source for modern history of Art of Memory
    d. Influenced by Rossellius, Romberch, Aquinas, Bruno

FIG. 10K
PRIOR ART

24. Francis Bacon (1561-1626)
    a. Used Art of Memory
        i. Believed in using active images to impress in memory
        ii. Principles of order and arrangement
    b. Wrote:
        i. Advancement of Learning
            1. Said Memory could be improved, used for practical purposes
    c. Believed Art of Memory used to memorize and later investigate
    d. Wanted to improve inventive logic
25. Rene Descartes (1596-1650)
    a. Wrote
        i. Discours de la method
    b. Had a great memory
    c. More occult than Bacon
        i. Rationalized occult memory
        ii. Lack of interest in imagination
    d. Disliked Lull
    e. Introduced quantitative application of Art of Memory as opposed to qualitative
    f. Goal: to provide universal art or method, based on reality that could be applied for the solution of all problems
        i. Kind of a geometric logic

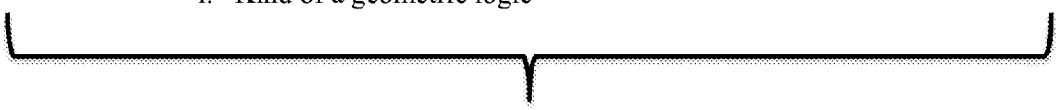

FIG. 10L
PRIOR ART

26. John Amos Comenius (1592-1670)
    a. Wrote
        i. Orbis Pictus (1658)
            1. Premier for teaching children languages by means of pictures, pictures arranged in order of the world, heavens, stars and celestial phenomenon of animals, birds, stones, etc.
                a. Original Pedagogic methods which made language learning enjoyable
                b. Children learned alphabets in all languages through images on a wall (solarian)
    b. Practical, original and valuable (ex. Learning languages)
27. Gottfried Leibniz (1646-1716)
    a. Created infinitesimal calculus – independent from Isaac Newton
        i. The universal language of system, final goal of Art of Memory
    b. Best example of survival of influences in Art of Memory (from lullism)
        i. Interprets Lullism with arithmetic
    c. Wrote
        i. De Arte Combinatoria
            1. Based on adaptions of Lullism
            2. Very like traditions of classical Art of Memory
        ii. Disputatio de Casibus In Jure (1666)
        iii. Dissertatio de Arte Combinoatira
    d. Goal: inventing a universal calculus using combinations of significant signs or characters
    e. Established notae as joining image of something sensible to the thing to be remembered (using Ad Herennium as basis) (also recalls 3 laws of Aristotelian association)
        i. Established notae as an alphabet (notae as natural as possible) resembles geometric figures like Egyptians and Chinese used before it.
    f. Goal: Message of universal love and brotherhood, religious tolerance, charity and benevolence
    g. Conclusion: Latest Art of Memory influence of current views: using Art of Memory would progress the sciences, lead to extended knowledge of universe, then wider knowledge of God, its creator and then a wider extension of charity, the source of all virtues.
    h. Rosicrucian aura with hermetic traditional marks and Egyptian and Chinese symbols

FIG. 10M
PRIOR ART

METHOD FOR CREATING A MNEMONIC EXPERIENCE

CROSS-REFERENCE TO RELATED APPLICATIONS

This application claims the benefit of provisional patent application 61/595,020, filed Feb. 3, 2012, which is incorporated by reference.

STATEMENT REGARDING FEDERALLY SPONSORED RESEARCH OR DEVELOPMENT

Not Applicable

THE NAMES OF PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The invention relates to mnemonic methods and mnemonic systems, and particularly to computerized systems and tangible items utilizing the mnemonic methods and systems. Examples of tangible media include computer-readable media storing computer applications, websites, online co-creation communities monitored by the mnemonic system, games such as card games, books, and curatorials at locations such as museums and theme parks or corporate offices.

2. Description of the Related Art

Due to the development of the printing press, humans, have erased, rested, weakened, and left unused their mental discipline and memory retention abilities. No longer requiring dependence on solely their memory, and being able to seek outside aid (i.e. books, words, and external means of storing information), many have weakened their individual minds at the opposite rate of which these external sources manage to keep their information.

As time has passed, technologies evolved, and methods of storing information progressed from floppy disks to CD-ROMs, USB's to external hard drives, and wireless transfers to Bluetooth connections, humans have weakened their minds and their ability to work independent of these external devices. Be it in work, hobbies, government, facts, stories, speeches, lessons, across the board possibilities in the knowledge spectrum have allowed people, with the aid of technology, culture, and dependency on external aids, to lose or dull the mind's ability to recall, store, and remember information in that specific order.

Simonides invented a mnemonic system in approximately 550 BC. The system built memories by combining them with a series of places or loci. It was developed extensively until the creation of Gutenberg's printing press. The second step in the early systems was the creation of shocking images to attach to the specific items the individual user wished to remember. The following step was the placement of these shocking images (i.e. memorable images) in the place or locus in the order one wished to remember it. The recollection part of these steps required a user to visit these places in their mind; starting in the beginning, middle, or end and working their way through or back in sequential order to recall everything the user wished to remember. The process required the repetition of this mental journey through the established place or loci in order to ingrain the images, words, or items into one's memory. In other words, the Simonides mnemonic system, as it progressed through time, taught users to remember things by going through an entire order sequentially (i.e. from start to finish in a sequential order). Simonides and the future contributors to the art also taught that to make a memory memorable that the image should be involved in an action. That is, the object should be moving or doing something uncommon in order for it to become memorable to the user.

In the early $17^{th}$ century, Johann Winkelmann made changes to advance the art. In 1648, he created a code to convert numbers into phonetic sounds in order to remember long series of numbers like the value of pi for example. In the 1870's, Hermann Ebbringhaus, the academic psychologist, was the first to study memory in labs. He concluded people have not significantly changed during the entire evolution of man. He believed the difference between a person in 2011 and a caveman is mostly their memory. Marcus Dwight created the Loissette system in 1887 but was considered a fraud. Dwight made his fortune before people noticed his inaccuracies. Psychology professor K. Anders Ericsson developed the skilled memory theory and explained how and why memory is improved upon through SWAT experiments. Harvard psychologist George Miller developed the theory known as, "The magical 7, plus or minus 2." The person that concentrated on the opposite of developing memory retention is Gordon Bell. This Microsoft scientist is part of a new movement in taking externalization of memory to logical extremes. It is sometimes described as the final escape from the biology of remembering. He keeps a digital surrogate memory and coined this concept as "lifelogging".

Many of the figures connected to the art of memory researched and promoted the use of one or more particular steps involved in the art of memory technique. All of the listed scientists, with the exception of Tony Buzan, were not widely recognized. Tony Buzan has researched mnemonic systems. This man developed and sold the concept of mind maps. Tony Buzan was the first to bring the concept of remembering through mind maps to the mass market. One of Tony Buzan's disciples is Raemon Matthews, a high-school teacher in the South Bronx, who taught his students Tony Buzan's mind-mapping concept of memorization. This group later went on to be coined "the talented tenth". The most recently acclaimed-to-fame man associated with the art of memory is Joshua Foer, the author of Moonwalking with Einstein.

BRIEF SUMMARY OF THE INVENTION

The invention encompasses a method for creating a mnemonic experience that causes an observer (i.e. a user) to remember information observed in the experience.

In addition, the invention includes products, services, and events that include the experiences produced according to the method. For example, the invention includes curatororial and thematic productions of experiences that are mnemonically enhancing. The invention encompasses media that includes the experiences produced according to the method. Examples of media include books, board games, music, films, and the like. The experiences can be embodied in digital media and devices that play the media. Examples include stored in electronic files on computer readable media. The invention includes media devices running and displaying the media such as wireless devices, smartphones, computers, tablet computers, and the like.

An object of the invention is to provide a system whereby experiences can be created and then observed in order to provide memories to the observer.

A further object of the invention is to provide a means whereby licensees of the method can create experiences that are certified by the licensor before distribution and/or expereince.

The system according to the invention is to be marketed under the trade name Mecubed. Mecubed is an acronym that stands for $(ME)^3$, which in turn, stands for Memory, Mind, Magnate, and Education, Entertainment, and Experience. The beginnings of these words are the three M's and three E's.

The mnemonic system according to the invention teaches people how to learn with a new innovative mind technique. The system improves an individual user's current memory of remembering by applying a method that is not daunting or exhaustible through a formulaic series of steps.

The mnemonic system according to the invention is a mnemonic technique that ensures memory retention through the implementation of formulaic steps catered to optimize an individual's retention, recalling, and recollecting capabilities. The mnemonic system according to the invention instills and teaches how to "Remember Right".

Through cross genres and cross disciplines while catering to every single type of demographic and secondary user breakdown, this fully integrated invention aids the user in memory retention.

The mnemonic system according to the invention is to be used as a comprehensive learning tool across multiple disciples, multiple platforms, multiple genres, and presented in multiple mediums, in the microscopic and macroscopic levels of a particular concentration and to be presented in the physical, digital, curatorial, thematic, and virtual worlds to result in a memorable experience.

The mnemonic system according to the invention is the ultimate recipe for rekindling the lost art of memory (a mnemonic system) by presenting it through a creative storytelling narrative lens. By innovating and advancing an outdated system, people can reconnect with their innate memory and not solely depend on external aids to assist their ability to recall/remember knowledge. The goal of these efforts is to strengthen significantly an individual's memory.

The mnemonic system according to the invention aims to teach and not tell, to learn and not download, to absorb and impress and not solely read and print, in an innovative interactive memorable manner; i.e. an entire experience.

The mnemonic system according to the invention aims to remove the crippling crutches with which we depend on external aids to remember, recall, and recite by empowering, teaching, educating, and elevating the learning experience to an innovative interactive memorable experience. The mnemonic system according to the invention strives to replace the weight of conventional education by purposely powering the inquisitive mind and helping people to "Remember Right".

Years of research, development, trial and error, and implementation of mnemonic techniques show there are many techniques for helping one to remember something. Examples of mnemonic techniques include but are not limited to rote memorization, familiarity association, rhymes, patterns, organizational skills, repetition, relaxation, retention, and competition concentration. The mnemonic system according to the invention is an updated and improved version of the ancient art of memory and its many progressions during the ages and does not deny the sporadic use of any of the above-mentioned methods of memorization but is founded on the formula presented in this application.

The formula presented below is composed of steps that produce an individual's retention/recalling memory, contingent on the particular selection of the method's chosen concentration. The results are based on an individual user's mind retention abilities prior to utilizing this invention. The steps can be broken down into sections or taken as their own individual steps. The order of the particular sections is important in producing the most efficient method of learning but the mnemonic system according to the invention can be restructured and still produce similar and effective results. By reorganizing and restructuring, the mnemonic system will not produce the most optimal results as following the formulated steps presented; however this does not impede doing so depending on the circumstances or concentrations.

The system can be repeated as many times as wanted to grow the individual's recall, recollection, and/or amount of information that an individual is able to remember.

A further object of the invention is to provide a standardized number of repetitions suggested per concentration to maximize the velocity of knowledge/information gain, but in doing so, stated in the previous and subsequent manner in the formula, it must be noted the results could vary widely.

The repetition of at least one complete progression of the concentration in its entirety is preferred. The progression of the repetition of a complete experience, a portion of an experience, specific areas, divisions, sections, rooms, or multiple repetitions through the same entire experience only strengthens the recollection of an individual per that concentration and the information presented. Experiences can be repeated in the same platform or across different platforms or mediums to produce more effective results. The repetition of the experience includes the repetition of the previous example but does not mandatorily have to include exclude experiencing the same concentration through a different platform, medium, or experience to produce results.

Not experiencing the entire experience may decrease successful retention and is not recommended. Results suggest a successful experience includes a minimum of one entire experience. Performing the steps of the method in different order is possible; however, the results are not as effective when the steps of the method are performed out of the order.

Experiences can be repeated in the same platform or across different platforms or mediums to produce more effective results. The representation of the palace can come across in multiple platforms, for example, but not restricted to: web, internet, print, interactive, software, 3D reality, augmented reality, physical, architectural, curatorial and thematic structures, and any visual representation of the image, classic, or contemporary method developed or to be developed, of a palace in its entirety or in is specific peculiarities (i.e. Particular but not restricted to sectors, rooms, areas, segments etc.) and the experience produced by the formulaic steps. The repetition can be a total of additional experiences, a portion of an experience, specific areas, divisions, sections, rooms, or multiple repetitions through the same entire experience.

The system can lead to reflections about information inside the concentration, the concentration itself, or the user individually. The results can be as broad as global reflections or as narrowly reflective as an individual's personality and goals creating tangible and intangible results.

The system can lead to observances about the details around the information. These observances can become theories, ideas, and concepts that are either innovative to a certain field or the first in the train of thought.

The system can also create new perspectives and points of views. The system can lead to respect and knowledge of concentration and inter-connected concentrations.

Respect and knowledge produce educated communication and the basis for furthering any particular interest: be it in the particular area of concentration or adapted and applied to another concentration.

New perspectives can become new fields of research, studies, developmental and experimental concentration fields or hobbies.

The below list is a shortened macroscopic list of the method. Preferred embodiments with more detail are provided below.

1. Select a Concentration
2. Gather Information
3. Research, Read, Annotate, and Determine Importance of the Information
4. Select Material to be remembered and place it according to a set manner
5. Create a REALly Imaginary Palace
6. Create a Primary Character
7. Create and communicate with Secondary Character's
8. Go through the Experience (Walk through journey, travel)

It has been discovered that establishing a partner in the journey makes the experience a more memorable one.

A basis for including a partner character as a teammate to whom the user can relate, compare, compete, and grow, is linked with improvement of retention capabilities.

The order of steps in the method can be changed or rearranged. However, a method that utilizes the steps in the order that they have been listed has been found to increase retention in the individual user. Using all of the steps, particularly in the order provided, has been found to be the best way to create memories that are retained by the user with the information presented.

This invention provides an innovative changed implementation of the art of memory technique, originally developed in 550 BCE by Simonides, which has been developed extensively until the creation of Guttenberg's printing press in which the prior technique lost its efficiency, its consistency and was abandoned as a method of remembering.

Though prior-art inventions, techniques, and methodologies have achieved a considerable amount of popularity and commercial success, there is an increasing need for a modified, innovative, and more efficient formula of remembering; one that spreads across multiple platforms and mediums, considering our evolution as a civilization throughout the years, while maintaining its efficiency and is adaptable to the technologically advancing world in which we live.

The mnemonic system according to the invention is a comprehensive learning tool whose usage can be across multiple disciplines, multiple platforms, multiple genres, and presented in multiple mediums, with microscopic and macroscopic concentrations presented in the physical, digital, curatorial, thematic and virtual, worlds to result in a memorable experience.

The invention includes a system for rekindling the lost art of memory (a mnemonic system/practice/methodology) through a formulaic system through a series of steps by presenting what is to be remembered through a creative storytelling narrative lens and implementing essential elements that are innovative and adaptive of our times and circumstances. By innovating and advancing an outdated system, humans can reconnect with their innate minds and memory and not solely depend on external aids to assist their ability to recall, remember, and cite knowledge.

A display is a person, place, or thing that teaches information to a user when the user observes the display. A display is created to teach information to the user. In the context of an art history example, a display could be a cave painting. The display could be the cold temperature in the cave that is chosen to make the user remember that the painting was made during an ice age. The display could be an actor or virtual caveman that communicates with the user.

"Contextually related character" means that the character is related to the information that is being taught. In other words, the character can be part of a story related to the story. Using an art history example, the character could be the artist or patron who made or commissioned an artwork that forms a display. The user can interact with the character to learn and to help remember information contained in the display (i.e. the art work).

An object of the invention is to aim to teach, not tell; to learn, not download; to absorb and impress, and not solely read and highlight, in an innovative interactive memorable manner or experience.

The invention aims to remove the crippling crutches with which one depends on external aids to remember, recall, and recite by empowering, teaching, educating and elevating the learning experience to an innovative interactive memorable experience. The mnemonic system strives to replace the weight of conventional learning by purposely powering the inquisitive mind and helping people remember right.

The below presented formula is composed of steps. When followed, the system produces an improved retentive state, whose results are measured on an individual user's specific memory and not to be compared to others who may have varying circumstances and contingent on the particular selection of the method's chosen concentration. The steps can be broken down into sections or taken as their own individual steps. The order of the particular sections is important in producing the most efficient method of learning but can be reorganized and still produce results that are educationally strengthening. Particular steps can be rearranged, slightly restructured, and moved around and have the results that are for the improvement of said individual's retention abilities per the concentration presented. Regardless, particularly good results are produced when the method is implemented in its ordered entirety to ensure effective memorable results in an individual's memory's retention abilities.

The method and system can be embodied in a variety of forms. The method can be embodied as a computer readable program in which a computer reads/is coded with the steps/instructions to display the information to the user in the monitored way. The computer can be a desktop computer, terminal, tablet computer, smart phones, or the like.

The representation of the palace can come across in multiple platforms, for example, but not restricted to: web, print, interactive, software, 3D, augmented reality, physical, architectural, curatorial, and thematic structures, and any visual representation of the image, classic, or contemporary method developed or to be developed, of a castle in its entirety or in is specific peculiarities (i.e. particular but not restricted to sectors, rooms, areas, segments, etc.).

This mnemonic system according to the invention is used as a comprehensive learning tool across multiple disciplines, multiple platforms, multiple genres, presented in multiple mediums, and focusing on microscopic and macroscopic concentrations presented in the physical, digital, curatorial, thematic and virtual worlds to result in a memorable experience.

The mnemonic system according to the invention is outlined below.

1. Select a Concentration
   a. Can be as general or detailed as concentration is chosen to be addressed.
   b. Can be as specific or particular as things, people, text, words, entire concentrations, and detailed or as broad as countries, religions, laws, practices, art, history, cultures, music, language, topics etc.

The first fully developed embodiment of this method, across multiple platforms is the concentration labeled as ART HISTORY (cumulative and can be further expanded on or condensed). A creative storytelling narrative has been written as well as the 2D and 3D architectural renderings, drawn to scale, of said concentration.

2. Information Gathering
   a. Involves gathering all accessible information regarding the specific selected concentration. The gathering of information can be done through traditional and non-traditional sources. (*Note: For example but not restricted to, books, autobiographies, biographies, diaries, chronologies, encyclopedias, articles, music sheets, sketchpads, reports, first person accounts, interviews, videos, movies, online databases, online communities, libraries, etc.)
      i. Additional to accepted and accessible methods of gathering information, if the concentration warrants it, it involves requesting permission for sealed/publicly inaccessible records, if it concerns knowledge for the selected concentration in Step 1.

3. Research, Read, Annotate and Determine Importance of Information
   a. Spend extensive time reading and researching.
   b. Take qualitative, quantitative, concise and detailed notes on pertinent information.
   c. If it pertains to a factual account where the topic will be stated as non-fiction, academic, factual, or the likes, verification, validation, and proof of facts must be used.
      i. If the concentration selected in Step 1 is subjective or controversial, subsection 3c does not apply and the users of this patent will select the importance of the information contingent on the goal of the concentration.

4. Select Material to be Remembered and place in set manner
   a. If the material to be remembered is an image, person or visual/audible object/image this becomes the object/image to be remembered. (For example, but not restricted to sculpture, paintings, monuments, people, material goods, images, graphs, music, sketches, elements, material objects and its likes).
      i. The object/image can or cannot be given a movement to associate with, determined by the users/owners of the invention and contingent to the circumstances within the concentration.
      ii. The object/image by means of an action can be altered or modified without intent to change the context of what the image/object represents (its elements and/or features included). Such action can be altered or modified by the owners of the formula.
         1. Intent to change must be regulated and controlled by owners/licensors of the formula. Licensees of the formula agree to the compliance and adherence of all previously and subsequent stated points in the formula.
   b. lithe object/image is not associated with a movement the invention creates its retention through the experience (ALL STEPS and in particular STEP 8).
   c. lithe object/image is given a movement such movement, determined by the owners of the formula and the adherence of all previously and subsequent stated points, must be something exceptionally based (for example but not restricted to the unusual, unbelievable, unique, great, dishonorable, surprising, shocking and the likes) In one embodiment, the regulation and ruling parameters are defined on a concentration case basis by defining the action given to an object/image while taking into consideration the specific niche target audience that will be experiencing said concentration. Owner/s and authorized licensees of formula would like to standardize, but in doing so, stated in the above manner, must note the results could vary widely.
      i. lithe object/image is ascribed a movement the movement will be one that adheres to the context of the object/image or be altered so that it benefits the efficiency of an individual's retention but does not dishonor or debase the context in which the image/object is presented.
      ii. The movement may be singular or repetitive so long as it adheres to the above-mentioned circumstances.
   d. lithe material to be remember is a fact, information, or something not already visually identified, then an image will be created by the owners of the formula and their adherence to the previously and subsequent stated points in the formula, to represent such fact, information or something not already visually shown.
      i. The image created may be directly or indirectly associated to said fact, information or something not already visually identifiable. Users/owners of the invention create an image that adheres to the invention's purpose and its goal to increase an individual user's retention capabilities.
         1. When creating above, certain stated image requirements must be met, elements not mentioned herein can vary across images but are only included if they adhere to the aforementioned and subsequent points in the formula.
            a. Image must be complete and viewable it is entirety. This does not account for a viewable 3D rendering but so that the image can be viewed entirely within a frame and any set individual moment.
            b. Image must be clearly visible so that entire image is seen unless experience garners otherwise which then becomes part of the experience and part of the concentration. (I.e. what is not clear is not clear purposely, whose purpose is defined with the adherence to the aforementioned and subsequent stated points in the formula).
            c. Image created must be visually presented in a cohesive manner applicable to the style, method and variants of the specific concentration.
            d. All characteristics, descriptions, and non-visual elements (for example but not restricted to speech, thoughts, mannerisms, personality, tendencies and non visual descriptive qualities) pertaining to an image/object have a purpose to either present and/or strengthen the visual image, serve the purpose of engraining the visual representation into an individual's memory and retention capabilities, and/or serve the alternate purpose of adhering to the aforementioned and subsequent rules in the invention or formula.
            e. Create an outline, form, or categorization system of all information in a set manner. (**Note: Set manner contingent on how and what the concentration's information demands which varies according to circumstances Detailed in 4i. and 4ii.)
    f. Place in the sequential order the above selected and established object/image you would like to remember.
      i. If it pertains to a factual account where the topic will be stated as non-fictional, academic, factual, or the likes, a chronological order or respected logical progression will determine set manner.
      ii. If the concentration selected in Step 1 is subjective or controversial. Subsection 4di does not apply and the users of this patent will select the set manner in a logical set manner always keeping and maintaining the efficiency of the formula herein.
        1. System is created so information is recalled in order and can be structured to be recalled at either the beginning and going through, the end and regressing in order or starting in the middle and going either forward or backward order.
5. Create REALly Imaginary Palace
a. Must meet certain elements in order to be effective (elements can be left out of the method but a majority must still be present in the creation of the REALly Imaginary Palace in order to guarantee an individual's successful and efficient method of recalling, remembering, reciting and/or retaining.
    i. Elements to create the palace should be:
      1. Architecturally Structured
      2. Must have a foundation, purpose, or layout that effectively conveys concentration's information and goal.
        a. Can be a REAL place
        b. Can be an imaginary created place
      3. Must be laid out, blueprinted (either/or/and 2d and 3D), created, drawn up, rendered, projected, virtualized, and analyzed.
      4. Can be an imaginary/created palace but have its scale finite without unknown areas, section or segments and no confusion of division between areas, segments, and/or divisions.
      5. Laid out, blueprinted (either 2D or 3D) and analyzed in a clear, concise, detailed manner to fit the standards established in step 4 herein.
      6. Each segment (typically recognized but not restricted to a room, particular area or individual segment) must be different from the previous or the proceeding (differentiation is important for success of system).
    ii. Can be reused for different concentrations if deemed permissible by patent's owner.
b. The representation of the palace can come across in multiple platforms, for example, but not restricted to: web, print, interactive, software, 3D, Augmented Reality, physical, architectural and thematic structures, and any visual representation of the image, classic, or contemporary method developed or to be developed, of a castle in its entirety or in is specific peculiarities (i.e. Particular but not restricted to sectors, rooms, areas, sections, wings, segments etc.).
c. Palace can be experienced multiple times to increase efficiency and capacity to remember greater amounts of presented information.
    i. This is done either through visual descriptions or presentation of palace in a memorable manner, adhering to the previous and subsequent stated points in the formula, be it through but not restricted solely to, verbal description and/or visual imagery.
d. Suggested experience length depends on concentration, retention, and repetition of the individual experiencing said stated palace. It is the decision of the owner/s of the formula whether to use a palace with simultaneous concentrations (keeping in mind repeating only unlikely concentrations with their potential to be experienced by the same user). (I.E. a same palace with simultaneous concentrations in fields that are opposites and would attract a different target niche individual audience).
    i. Applicant does not believe in this use as the result's efficiencies lower drastically. Not as effective with multiple concentrations inside the same palace at completely independent times but can have exceptions to this if the situation calls for it. Please understand owners of formula would like to standardize, but in doing so, stated in the above manner, must note that results could vary widely.
    ii. This does not restrict the study of two concentrations independently, contingent on two different REALly Imaginary palaces being implemented.
    iii. This also does not restrict the study of two concentrations in the same palace if the owners of the formula deem it permissible, always keeping in mind an individual's efficiency and retention levels.
      1. It is possible to develop two different concentrations on one same palace so long as they are presented independently of each other and that attract two different target audiences who may or may not experience both concentrations.
      Handling and experiencing two exact palaces will reduce the ability of retention drastically, regardless of the difference between concentrations if an individual chooses to experience both concentrations at different times.
    iv. Different concentrations can have same palace architecture and elements but be experienced differently so it would produce a different experience in a palace. It must be noted that results could vary widely in this case.
      1. I.e. One palace can be used for geography and again for economics, it can be independently introduced at a simultaneous time, but is contingent upon the individual's selection and time of experience.
      2. Avoid noises or distractions that hinder, cripple, or disturb the learning experience while going through the experience.
e. People, noises, and other elements inside the experience that serve an educational and retention focused purpose are implemented when their presence strengthens and/or fortifies an individual's retention capabilities.
    i. The presence of people in particular segments/area/rooms is used to represent significant people depending on the selected concentration's need of the presence of someone who changed history for the selected concentration's specific area/room/segment.
      1. The person's representation shall adhere truthfully to whom the person is with subjective methods of communications.
        a. A person will only be present if their presence is educationally beneficial to the particular area, section, room, division, portion of the concentration and conclusively therefore of the experience.

2. Noises in the form of music, silence, or any form of auditory elements shall adhere truthfully to their purpose and position dependent on the concentration.
   a. If the experience requires noise for efficacy, noises will be implemented. If silence is required for efficiency, no noise shall be placed within the experience.
   b. The noises in the form of music, silence or any form of auditory elements shall not be changed or modified from its original context.
3. Other elements (e.g. actions, tools, artifacts, or any form of tangible asset whose benefit outweighs its hindrance) are variable elements whose productivity aids in the experience rather than taking away from it, therefore garner their usage or appearance in the particular location inside the concentration.
f. If at any time, the people, noises, or other elements implemented cause a hindrance, their presence will be removed by owners of the formula and their compliance and adherence to the previously and subsequent stated points.
g. The palace must be well lit.
   i. There must be clarity to see the entire section/area/room at all times unless experience garners otherwise which then becomes part of the experience and part of the concentration's specific section/area/room.
   ii. There must be space between elements or visual representation of information put forth to be retained so as not to appear cluttered but not so spacious as to appear distant beyond recognition. This space is determined by the users/owners of the patent and can be anywhere from two to three feet apart to larger distances between each other.
      1. There must be an identifiable distance, mention of established distance is not necessary for the purpose of efficiency unless the presentation of such distance is a contributing factor to the individual's retention.
      2. It is not permissible to have an infinite amount of space among object/s, people/s or element/s to be remembered as it would not adhere to the abovementioned circumstances.
6. Create a Primary Character
a. Alongside the user, the primary character is to become a magnate master mentor.
b. Primary character is created for every concentration, this partner character becomes greater, almost heroic while learning valuable information, confronting challenges, defeats, adversaries, demons, and adversity and ultimately ends up either victorious, completely changed and or a learned individual.
c. Primary character can be the same as previous concentrations so long as their persona would benefit efficiently from the experience and concentration.
d. Primary Character is created to adhere to the previous and subsequent stated points in the formula, whose visual image is warranted by the style, method or form of presentation of the concentration.
7. Create and communicate with secondary character/s.
a. A secondary character/s (or partner character/s) is created for a specific area/section/segment/palace within a concentration; the partner character (secondary character/s) aids in strengthening an individual's retention abilities. Individual experiences can be almost heroic, ultimately always learning, valuable, beneficial, challenging and changing. These secondary characters (mentors/teachers) are positioned per palace/segment/area of section/room of the REALly Imaginary Palace, but are not mandatory. Only created if their result is deemed, by owners of formula, beneficial to the individual's retention capabilities. (The secondary character is recognized and seen as a mentor, teacher and/or educator as the purpose of his presence is to impart knowledge upon the primary character and ultimately the individual user).
b. The secondary character may be momentarily accompanied by another tertiary character who's presence guarantees a stronger impression in the memory and whose presence is for less than 15% of the area's/section's/room's experience.
c. The user along with the primary character experiences and learns through the teachings and communications of the secondary character (i.e. Mentors/teachers/other elements (e.g. iPod, phone, iPad, watch, necklace, ring, any form of communication) to aid in education/learning/retention capabilities when applicable to concentrations.
d. All secondary characters mold to benefit the concentrations.
   i. Secondary Character is created to adhere to the previous and subsequent stated points in the formula, whose visual image is warranted by the style, method or form of presentation of the concentration.
8. Go through the Experience (Walk through, journey, travel)
a. Through a creative storytelling narrative lens, the character along with user, experiences the palace (therefore the concentration and its elements as well as its entirety) (i.e. each palace/section/segment/area with communication encounters with mentors/teachers/or other elements to educate in an interactive, innovative, and memorable experience) to impress and ingrain experiences and, more importantly, the concentration's previously established outlined knowledge) (STEP 4).
b. The experiences are scattered with a spontaneous and sporadic array (still in consideration to the chronology as mentioned in 4.f.i and the general sentiment of subsequent 8.c) of, but not solely restricted to, challenges, changes, pauses, passes, actions, shifts, shocks, tests, presentations, and lessons to aid in an individual's retention efficiencies.
   i. This allows for the use of above mentioned (8.b) elements throughout the palace but is not a requirement per section, area, division, room of each palace.
c. The experience is catered, created, and formulated to be sequential and in an established progression to ascertain its efficiency.
   i. This does not permit an individual user to jump around areas.
      1. The jumping around or change of experience's order (pertaining to room, section, area, division) is permissible only after an individual has gone through the experience (STEP 8) in its entirety.
      2. Selection to return to a specific/individual/personally selected room, section, division, area by an individual user of this experience upon completion of entire experience is permissible but not compulsory or detrimental to an individual's future retention capabilities.

The system according to the invention differs from the prior art in the following ways.

The invention creates a "universal method of communication/alphabet" in a specific concentration that develops into a universal language/method of communications. Across borders, the universal method of communication/alphabet becomes a method of communicating based on shared, pre-established terminology and experiences. The terminology and experiences could be the result of the grouping of words and/or images, stills, and/or video and of the specific concentration's experiences or pre-established terminology. This said, the universal method of communication/alphabet may also include the primary and secondary characters as well as any other elements integrated in the experience. This method of communication joins the vernacular and the academic methods of communication and can spread across cultures, countries, and language barriers as a method of interactivity/interaction and conclusive communication. For example, when one person says a phrase that triggers a memory from a mnemonic system that the user observed, the phrase will trigger the same memory in other users who have used the same mnemonic system (i.e. palace) whenever the other users hear the phrase. In this way, the mnemonic system can be used to create memories and a method of communication that are shared and related by many people. For example, when one says a particular phrase, the phrase will trigger a memory in the users of the system. The memory being triggered is shared from user to user.

The mnemonic system according to the invention presents/integrates a primary character, per concentration, to accompany the user along the experience. The character is present for at least seventy five percent (≤75%) of the entire experience but can be absent from specific section/areas/segments if the concentration's experience and technique benefit from such. This is applicable to the efficiency of the concentration, association to/of the user and the information, and entertainment of companionship in the particular concentration. This "mentor figure", which is implemented in the presentation/creation of the experience (be it curatorial, thematic, written, verbal, physical, augmented or presented), has not been implemented previously. In the co creation aspect of the application of the technique, such primary character will only be added after the palace is completed and closed, permitting no further contributions. Nevertheless, having company while experiencing a learning journey in these circumstances has never occurred or been implemented previously in said manner. The companionship of the main character and user in the invention's experience increases productivity and retention. The "mentor master magnate" figure implants instruction and the relationship of companionship instead of the status relationship between teacher and student, elevating the user to produce a memorable experience. This point is in correlation with the state of the art of memory prior to the invention of the instant application.

The mnemonic system according to the invention is the first to create and communicate with (a) secondary character/s in this process, in combination with all of the afore and later mentioned circumstances. Prior-art methods do not implement secondary characters. When it is beneficial to the particular entire experience, the invention/creation of the secondary character integrates retention ability and the individual user's experience with a secondary character element. This does not mean that in some cases there will not be a secondary character. The implementation of a secondary character will be used if the implementation does not hinder in any way the effectiveness of the technique outlined in the formula above and is determined a beneficial factor of added value in an individual user's memory and retention capabilities.

The system creates memorable images instead of letting the individual imagine his or her own. A user's flexibility to create his or her own images makes a communication platform impossible. By having the system create the image, the system produces an effective memorable image, one to fit the concentration, the information, and the retention in the memory, and one that creates a universal method of communication.

The introduction of preconceived, designated, developed, selected, and specific images establishes a habit. This particular habit, developed in the inventions manner, is memorable and ingrains itself in the subconscious level of an individual.

The prior art does not teach to create images for the user's suggested implementation of the technique. In the prior-art, images were created for visualization. However, the images created for one user were never used for another user. In contrast, according to the invention, the mnemonic system provides already-created images to the user. In the co-creation medium/application of this invention, it selects, through the invention's established formulaic steps and its circumstances, which image, submitted through co creation, is best to represent the information. This allows the same images to be supplied all users to create a "method of communication or shared language" of memories.

The system selects objects/images to be remembered but can also be the exact object or image to be remembered. This is something the prior art does not teach or present to the general public as is previously mentioned in the above and below differentiating elements of this invention in relation to the prior art.

By allowing the object/image to be remembered to be the exact object or image selected, (permissible at times to be modifiable or varied if context and herein mentioned steps permit) the mnemonic system according to the invention distinguishes itself from all prior art.

Regarding material to be remembered that is fact, information or something not already visually identified, the mnemonic system according to the invention is the first to create an image for the user (this differentiating circumstance mentioned among the distinguishing differences of the former art). By the co-creation application of the invention, the mnemonic system is the first to select and approve the image, contributed in the co creation platform that will serve as the image.

The mnemonic system according to the invention varies from the prior art per the selection of no associated movement to the object/image. The system according to the invention utilizes the experience (Step 8 mentioned herein) as the primary retention factor.

An individual user's flexibility to create the images brings forth many hindering and crucial factors that can affect the results/circumstances around the technique. By removing the user's flexibility, they system instills an image's memorable retention in the individual user's mind and conclusively increases successful memory retention capabilities.

The mnemonic system according to the invention creates an entire experience/world whose objective is remembering though the combination of mnemonic techniques, the before and aforementioned and the combination of the herein formulaic steps.

The mnemonic system according to the invention is the first to develop the process and implementation strategy for the co-creation application of the invention. Creating an architecturally created foundation/blueprint and then allowing the people to contribute through a standardized method (outlined below) of submission and approval, at all times adhering to the defining factors stated beforehand (i.e. a license agreement). People are then able to fill palaces through contribution. Said contribution is a mix of information and images, information whose legitimacy has to be validated and approved through the co-creation approval process (i.e. the license agreement), and images whose ownership must be credited and never misrepresented. This application is outlined below.

Mecubed owners or registered licensees of the invention choose a concentration. In a platform according to the invention, three palaces are independent and simultaneously developed at a time-displayed equally designed, equally coded, uniformly across these three. The three are designed according to a set style but adhere to a shared visual requirement, i.e. cartoon, anime, simulation, etc.

Developers and registered licensees define, with specialists, divisions (# of rooms, displays per room) and establish a template to use across the board. The template can change as trends change but uniformly all the same except for certain applicable variables per concentration like the number of items per room—example every room in concentration can be ten items only or can be personalized per room depending on circumstances determined by creative and concentration specialist) to present on the co-creation application platform, which can be online and/or offline.

Mecubed owners or registered licensees create (with a combination of architectural illustrator/s, creative, interior designer/s, animators, coders, etc.) structurally constructed empty palace/s (no contents inside). A definition of the concentration is presented alongside this, each particular segment/room/division/area with its characteristics establishing rules and requirements of any future contribution are also presented) (Note: *Creative and Specialist establish maximum number of images per segment—can be uniform per room per concentration or varied, dependent on concentration) (Note: *Anything outside of these set rules and requirements will not be deemed acceptable and immediately denied if not deemed appropriate by Mecubed owners of registered licensees).

Owners and/or licensors present the aforementioned developed co-creation application to users. This presentation is accompanied with a description/introduction of the concentration, the parameters it is being presented in, and the same for the specific segments/areas/rooms. It is accompanied with the rules for submission/co-creation. The licensees are allowed to submit 1 fact/artifact at a time (once signed into the co-creation community—having verified their identity) (which can be person, place, thing, word) to concentration. (Note: A cap can be placed per contribution per person to 'X' amount of fact submission per individual to weed out garbage immediately or allow for endless contributions per person.

The program, component, coded approval process goes underway. This process can be the already encoded in the algorithm/formula coded and no outside manpower necessary (contingent on the concentration and the parameters of the concentration within the co-creation application of the invention). The process may also be a combination of help from algorithm/formula to weed out large masses then followed up by Mecubed owners or licensees of the invention co creation team to verify and finalize the process.

The submitted information is then approved or denied, the individual user is notified.

If it is denied, it will not be included/presented within the co-creation platform stated palace.

If it is approved, the fact/contribution will be placed in it is correct segment within the concentration/palace in construction. (Seen as a mark/brand/symbol/star/asterisk/customized image developed in house when one chooses to see individual segment inside palace, seen as a note/star/mark when looking at entire palace as an approved item.

The users will be presented with said fact and will be able to submit (through the co-creation community) an object with one movement (open for creative interpretation and presentation but must be a singular object or mass with a singular action-action may be repetitive but must be visual) to concentration. (Note: A cap contribution per person can be placed to weed out inapplicable information immediately or it individuals may be allowed to submit endless contributions per person (either initially or all throughout) (contingent on established premises aforementioned which are based on the concentration at hand).

Note: Object and action must be submitted in unison, immediately denied if solely an object or solely an action.

The developed method of presenting the object with action can be 1. Two sentence description of object an action—cap at two sentence—harder 2. Visual Sketch 3. An Animation 4. A Picture of previous individual experience. Ownership of images must be cited if the image does not pertain/belong to the individual submitting it on the co-creation platform.

The program, component, coded approval process goes underway. This process can be the already encoded in the algorithm/formula coded and no outside manpower necessary (contingent on the concentration and the parameters of the concentration within the co-creation application of the invention) but is a different process, component, and coded approval process than the fact submission mentioned above. The process may also be a combination of help from algorithm/formula to weed out large masses then followed up by Mecubed owners or licensees of the invention co creation team to verify and finalize the process.

The submitted information is then approved or denied, the individual user is notified.

If it is denied it will not be included/presented within the co-creation platform stated palace.

If the information is approved, it will be presented to the people within the co-creation community. Said approved Image (representing previous approved fact) will be placed it is correct segment/area/room within the concentration/palace in construction. This will be visually seen when you choose to view the individual segments/room/area inside palace. It will be seen as a mark/brand symbol/star/asterisk/customized image developed in-house when looking at entire palace as an approved item).

Owners or licensors will specifically place the image in an exact location in the segment within the palace so that it adheres to the mentioned formula presented above.

When people see the image presented on the co-creation community, its location is inside the segment of the palace to scale. The location of the image and the image itself with the fact embedded into its object will not be changed once placed. (So as to adhere to the Mecubed formula mentioned herein).

Mecubed owners or licensors will deactivate the submission process per each individual room/segment/area upon the completion of the 'X' (previously) established images available per room established above. The room/segment/area remains fully viewable just not changeable by people or owners or licensors.

Note: All other incomplete rooms/segments/area will remain open for submission.

Upon entire co-creation closure of the rooms/segments/areas within the palace, the palace will be deactivated co-creatively but still fully viewable on the community/platform.

By allowing the association of movement to such selected object/image, the mnemonic system according to the invention is again different from the former procedures of the prior art as former art mandated a movement with suggested circumstances.

The invention contrasts prior-art systems. The prior art taught a system that focused on remembering certain things in one particular platform. The prior-art systems did not and do not teach systems that can be applied on concentrations on various platforms or across various mediums for the retention capabilities.

The system according to the invention teaches a combination of elements of a learning process taken from disparate prior-art teachings and its innovations, evolution and varying contributions through the ages, none fully encompassing and creating a sound, encompassing, singular method or technique.

The invention can include a combination of senses to ingrain a memory. This includes, but is not required of, each experience, segment, area, or study of concentration in its particular divisions or its entirety: for example, the utilization of the five senses: sight, touch, taste, smell, and hearing. The more senses are incorporated into the technique, the more effective the system is in creating memories. In an embodiment of the method utilizing current computer technology, the utilization of all five senses (i.e. smell, taste, and touch) is difficult. Still, by including as many senses as possible, the results for an individual's retention capabilities are improved. Real world embodiments such as a theme park or museum setting (for example but not restricted to these physical established experiences) can be used to create embodiments that include all five senses. Customized services rendered as an application or part of the formula, can be used to create embodiments that include the five senses as well.

The invention is the first in this art to concentrate or use the technique in a particular concentration, specifically referencing the current innovative technique outlined in the formula.

The prior art focused on the state of the art's history, the people associated in its study, and mostly what has happened in the art of memory's personal timeline and how it is to be applied if an individual uses it for personal needs. The prior art focused on proving, disproving, arguing, or discussing the state of the art instead of applying it to, in this case, beneficial learning and educational goals/concentrations/objectives. By focusing on the technique's history, the prior art dimmed the focus on the actual application of the method.

The system focuses on implementing the technique into credible and applicable streams of communication, retention, and the remembrance of information to make what is being retained (the purpose of the technique) an educational and purposeful one.

The system is the first to apply the previously-described memory technique to educational/learning concentrations/topics and not just chosen discrete spontaneous topics, genres, to demonstrate its retentive abilities/results. This does not mean that the system cannot be successfully applied to specific applications such as commodities, luxuries, hobbies, or passions (i.e. subjective concentrations or information).

The prior art focused primarily on trivial resources and knowledge to demonstrate its results. The prior art would elaborate extensively and over explain through repetition or attacks why it is the art was either effective or destructive, never specifically applying it to pertinent/relevant implementations and presenting it to the general public.

The system is the first to add a creative storytelling narrative (lens/perspective/presentation) to the improved memory technique as embodied in the previously-described method. The invention combines the communicable philosophy, approach, and presentation of the method and implementing elements such as a storyline, setting, character, secondary characters, plot, events, drama, epic wins, tragic fails, short term and long term successes and failures, climaxes, up and downs, internal and external conflict. The invention combines individual elements such as creativity (and not just methodological), storytelling (and not just presentation and reiteration of information), and narrative (not just combined sentences) with the technique. The invention is the first formulaic memory technique in the history of the art of memory that is executable on multiple platforms and can be experienced on more than one platform at the same time. The system can be experienced by an individual user multiple times in one platform and multiple times across multiple platforms. The art prior to this spoke of applying it solely to one concentration.

The prior art spoke of applying but never reiterated or presented the application examples past macroscopic general definitions/scopes/levels.

Having a developed system makes the creation educationally promising to improve/increase an individual user's current ability to remember what is being presented. This does not mean an individual user's memory will increase all around. The system improves retentions of the particular concentration being experienced and is contingent on experiencing at least one entire experience in order to insure an increase in an individual user's memory retention to the particular concentration at hand.

The mnemonic system according to the invention is the first to establish, develop, and outline a formula to apply to multiple platforms, concentrations, mediums and representations (visual and mental) of the implementation of the technique to reach each individual user the same.

In accordance with a further object of the invention, a method and system for co-creating of content is provided. Contributors can draft new content according to the framework of the invention. The draft content can be reviewed by a person that certifies the content or by a software/code that verifies the information submitted. Certifying content ensures quality content and prevents a fracturing of a common experience that can be shared by multiple users.

The mnemonic technique, in correlation with the art of memory and its prior history, is the first to implement the game framework and mentality of play/experience. The use of gaming psychology in the application of the art of memory mnemonic technique/system is a new method of approach that combines the art of memory and embodies the method within a gaming environment/framework/concept.

The mnemonic system according to the invention is a comprehensive learning tool whose usage can be across multiple disciplines, multiple platforms, multiple genres, and presented in multiple mediums, with microscopic and macroscopic concentrations presented in the physical, digital, curatorial, thematic and virtual worlds to result in a memorable experience.

The mnemonic system according to the invention aims to replace the weight of conventional education by effortlessly elevating learning through an innovative interactive experience. The mnemonic system teaches to Remember Right.

The system can be used to remember an array of information. The system can be used to remember historical facts (whose information can be verified). The system can be used to memorize information like an anatomy lesson, a poem, client information, product information, or a speech so long that it adheres to the above stated circumstances of the equation. Such usage is monitored on a sequential basis and deemed acceptable by owners of this formula.

The described systems and techniques can be implemented in electronic circuitry, computer hardware, firmware, software, or in combinations thereof, such as the structural means disclosed in this specification and structural equivalents thereof. This can include a program operable to cause one or machines (e.g. a signal processing device including a programmable processor) to perform operations described hose purpose includes the co-creation application of the technique. Thus, program implementations can be realized from a disclosed method, system, or apparatus, and apparatus implementations can be realized from a disclosed system, program, or method.

Similarly, method implementations can be realized from a disclosed system, a computer running a program, a computer program on machine-readable media to instruct a computer. The method can be implemented in a physical, virtual, audio application of a book, a game, or a curatorial experience. The method can be embodied and performed in a physical place like a museum, library, or park. In addition, the method can be embodied in a virtual setting, including but not restricted to a computer display.

The method according to the invention can be utilized in an educational setting, for example, an art history lecture. A book following the guidelines of the system can be provided to help a reader learn and remember information regarding art history. Similarly, a virtual place for learning art history can be created using a computer. As a user experiences the virtual place, the user is exposed to experiences that cause the user to learn and retain the art history information presented. Likewise, a real (i.e. non-virtual) place can be configured in a museum or park or any permissible physical convertible space to allow a user to travel within the place and to face experiences causing the user to learn, remember and retain information regarding art history in this particular case.

Other features of the invention are set forth in the appended claims.

Although the invention is illustrated and described herein as embodied in a mnemonic system, the invention is not limited to the details shown because various modifications and structural changes may be made without departing from the invention and the equivalents of the claims. However, the construction and method of operation of the invention together with additional objects and advantages thereof will be best understood from the following description of specific embodiments when read in connection with the accompanying drawings.

BRIEF DESCRIPTION OF THE SEVERAL VIEWS OF THE DRAWING

FIG. 6 is a table showing the steps of the method shown in FIG. 5

FIGS. 7A-7H were canceled.

FIG. 8 is a table showing the steps of a method for co-creation according to invention.

FIGS. 9A-9M are hierarchical views showing a history of art according to the prior art.

DETAILED DESCRIPTION OF THE INVENTION

Figure 1:
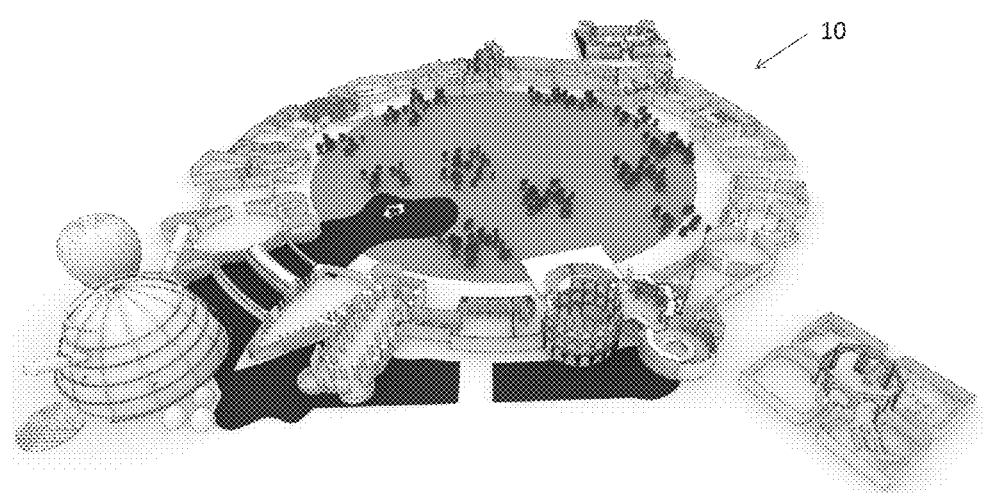
FIG. 1 is a perspective view showing a virtual palace for learning art history according to the invention.

Embodiments of the invention are described below and are shown in the figures of the drawing.

Figure 2:
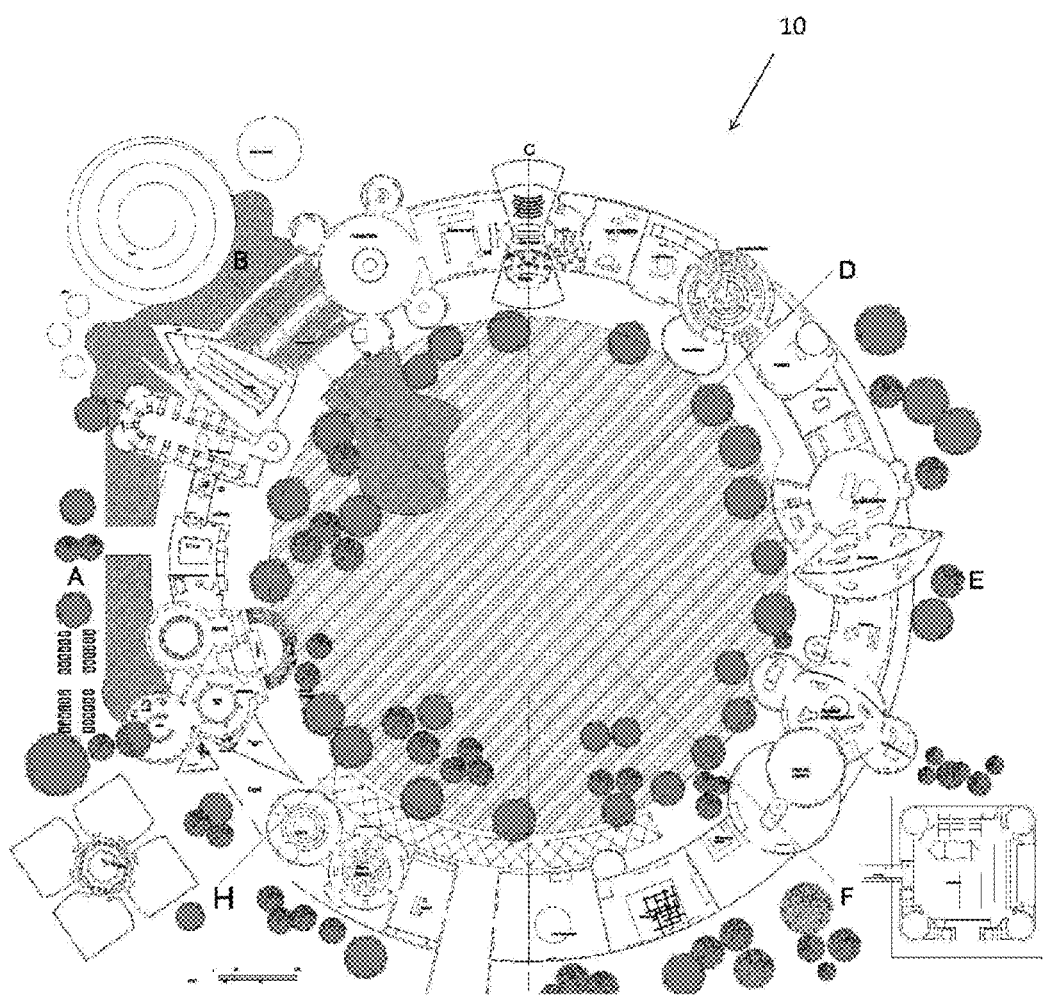
FIG. 2 is a plan view of the virtual palace shown in FIG. 1.

FIGS. 1-2 show images of an entire virtual palace 10. The palace 10 is an embodiment created by an application of the formula according to the invention. FIGS. 1-2 are a comprehensive, compact, and detailed example of the invention that has been developed and applied to a specific concentration. The palace 10 can be developed in different mediums, platforms, languages, products, and services. In the embodiment, the concentration selected is art history. The scope is the chronological or sequential presentation of art history. Chronological/set manner/order is presented sequentially and defined by time and/or time periods. Art history is defined by art in relation to known and sometimes hidden history and facts. In this embodiment, the topic is a real one but its presentation has been put together in a fictitious manner to adhere to the formula of the invention.

Figure 7:
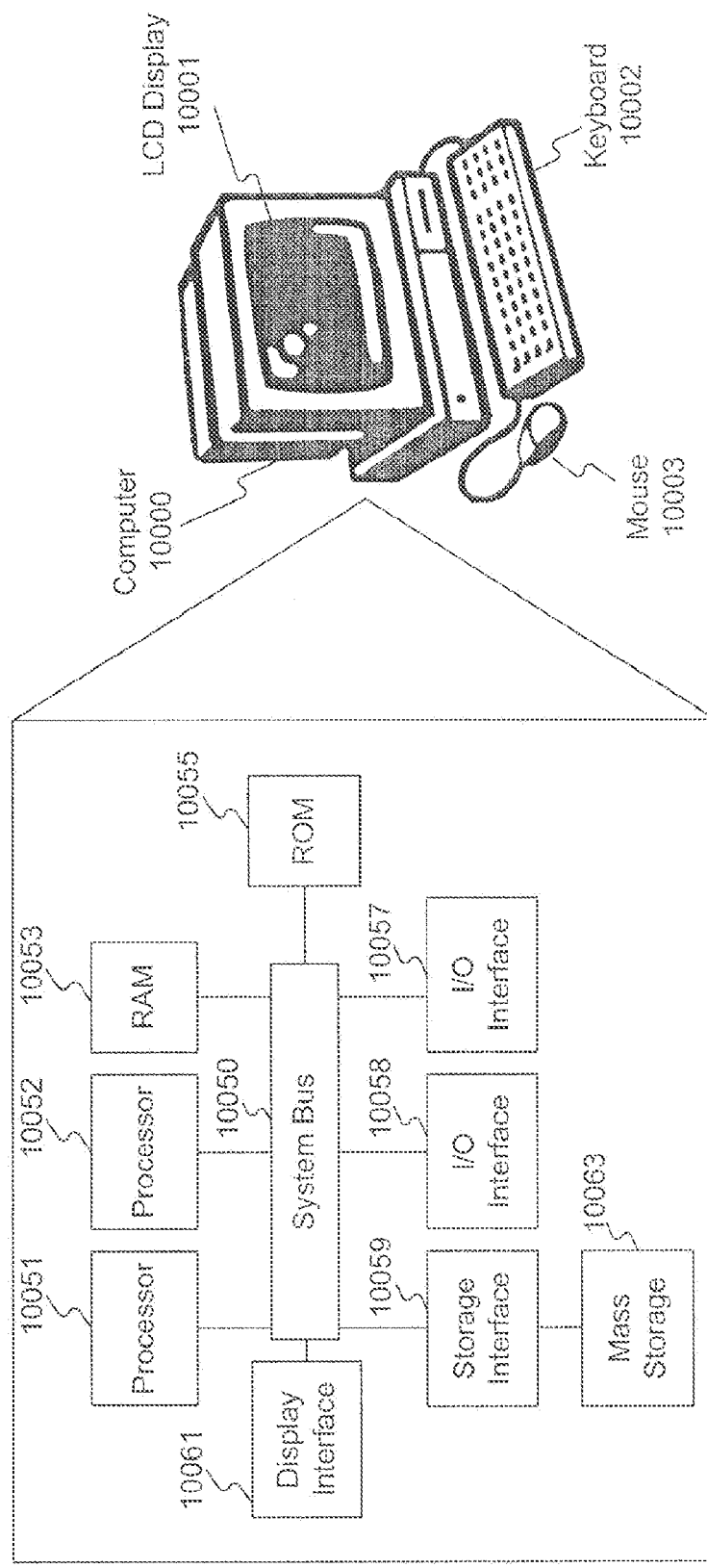
FIG. 7 is a schematic view of a computer according to the invention.

The palace 10 can be real or virtual (i.e. created using computer-generated virtual reality), presented via multiple platforms or in physical forms. In one embodiment, the palace 10 is an artwork that has been architecturally rendered/created in 2D and 3D formats, and has been drawn out. The palace 10 could be drawn for use in a book, card game, or tangible game, theatrical or curatorial experience. In another embodiment, the palace 10 can be presented as a co-creation social networking platform available to an online community. Through co creation multiple palaces can be developed in different concentrations. In another embodiment, the estate can be a virtual/3-dimensional/augmented reality model generated on a computer 1000 as shown in FIG. 7. The palace 10 can be a computer program on computer readable media that instructs a computer 1000 to display a virtual representation of the place. In another embodiment, the palace 10 can be physically built and manifested (traditionally, technologically, physically and/or in a curatorial manner created). The palace 10 can be embodied in a theme park, as a play or show, or at a museum (i.e. a curatorial/thematic). Regardless of the medium, the palace 10 adheres to the formula and its circumstances mentioned herein. The drawings show one embodiment of a palace 10. The embodiment is an example and should not be used to limit the scope of the invention.

The system can be used by students, institutions, corporations, individuals or advertisers who want viewers to remember and retain information about what is being presented. The system can be licensed to allow licensees to create their own content to be used by the licensor or by third parties. In addition, the system can be licensed to others for showing of the licensor's content to third parties.

FIG. 1 shows a preferred embodiment of a palace 10 created according to the method to help a user with a (virtual or real) presence in the palace 10 to remember and retain what the user observes and experiences in the palace 10.

Figure 5:
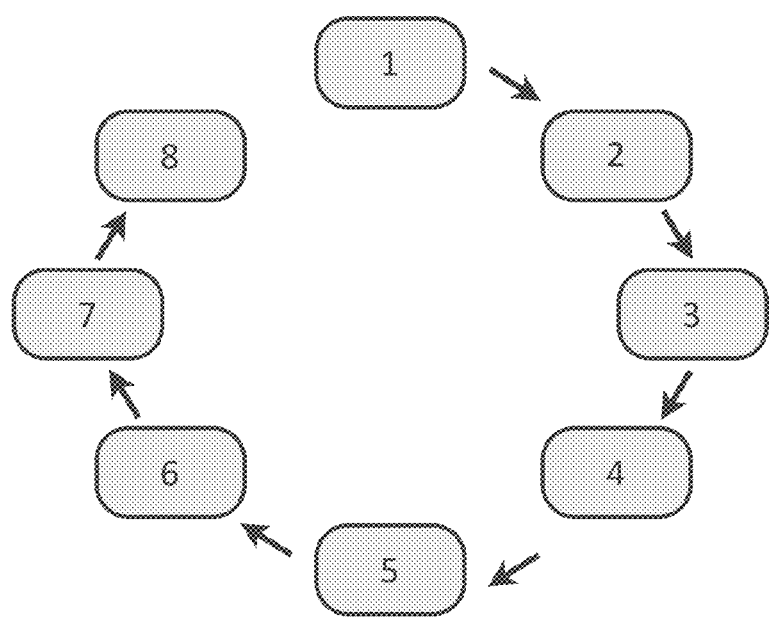
FIG. 5 is a flow chart showing a preferred embodiment of the method according to the invention.

As shown in FIGS. 5-6, the following steps and their detailed circumstances, apply the method to create the palace.

1. Select Concentration: For this example, the concentration is art history.

2. Information Gathering: The estate and respective rooms have been created after research, both through traditional, digital, and non-traditional methods.

3. Research, read, annotate, and determine importance of Information: for this embodiment, the research suggested to present the concentration (art history) in the periods. In particular, one period is assigned per room/segment/area within the palace. The order/sequential process/set manner has been defined by years (increments of time). Putting different periods in different rooms distinguishes the periods and differentiates them in the mnemonic process/technique/method. Occasionally, two or three periods may be grouped together for a mnemonically stimulating purpose, one who's benefits for grouping periods outweighs their hindrance.

4. Select material to be remembered and place in set manner: Due to the size of the concentration and the size of the particular period's information selected to be remembered, specific images have been selected based on their popularity, rarity, ability to adhere to requirements of the formula stated herein, and intrigue to the particular period, all aiming to be memorable pieces of information. Each piece is placed inside a room (which represents a period in this concentration), which is placed inside the palace/castle (which represents a concentration in this case art history).

5. Create a REALly Imaginary Palace: For this embodiment, the imaginary palace/castle has been drawn and architecturally rendered to scale in order to create a virtual, physical, digital (online and/or offline), curatorial, and thematic experience. The palace adheres to mnemonic remembrance. The palace is circular on the belief that history repeats itself. However, the circle is open under the supposition that we have not finished writing history. All historical knowledge, regardless of levels in the palace/castle, are placed on the first floor, significant interconnectivity and all walls are scaled to a set dimension height, twenty (20) feet high, to guarantee the memorable implementation of the entire palace/castle in an individual's memory.

6. Create a primary character: For the purpose of this entire image of the complete REALly Imaginary Palace and in regard to the book that has been written, the software application, and further products and services being developed, a character to experience such has been created. The character is created, rendered and selected in order to impress, engrain and imprint the information for the individual user experiencing the room (period) and castle (selected concentration) and for the benefit of the individual user's retention capabilities.

In the case of the formula herein, the palace 1 shown in FIGS. 1-2 adheres to the method and it is the visual application of the formula in micro and macro scopes of the technique or mnemonic practice.

Figure 3:
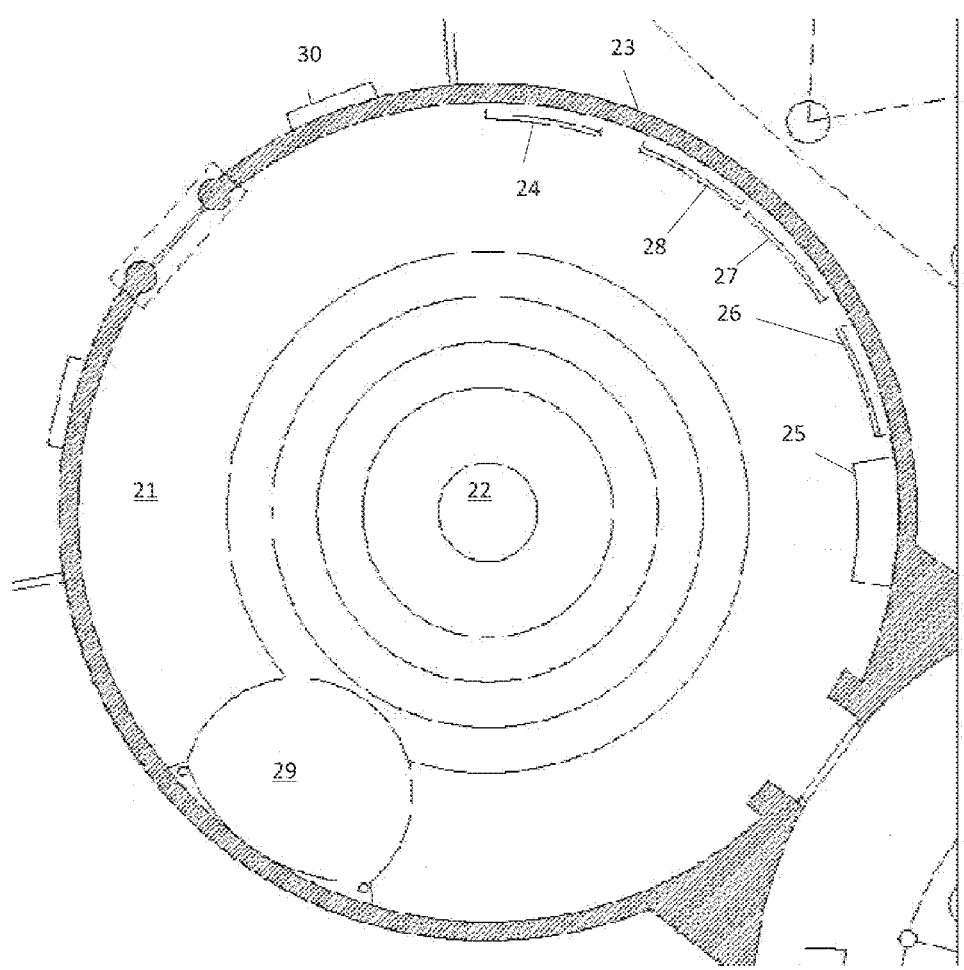
FIG. 3 is an enlarged, partial, plan view of a room of the palace shown in FIG. 2.
Figure 4:
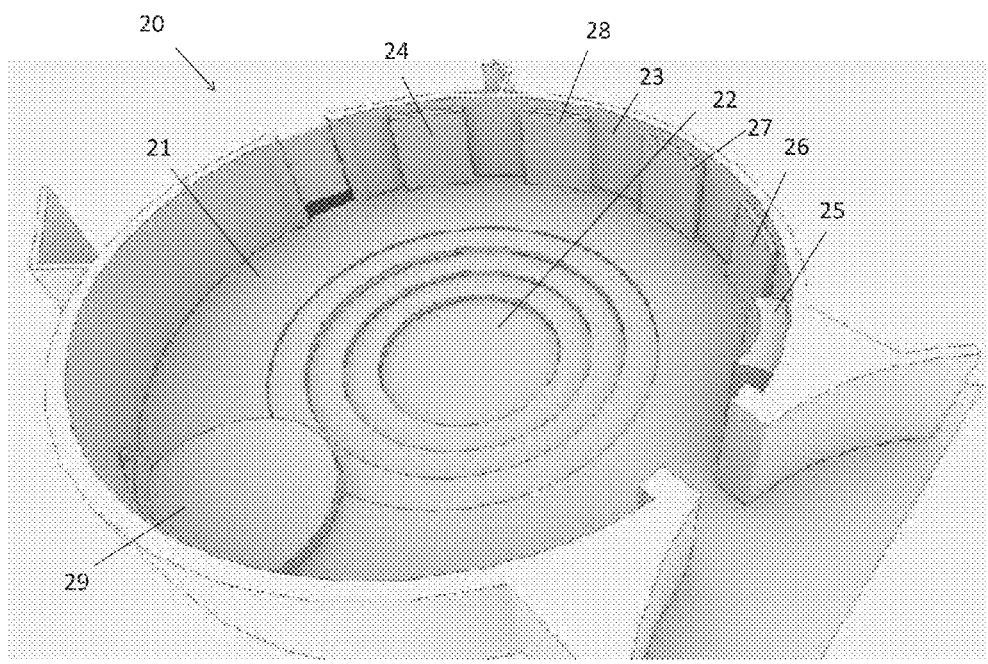
FIG. 4 is a perspective view of the room shown in FIG. 3.

In FIGS. 3-4, the room 20, per the art history concentration, which is developed and shown, displays images that are of the cave art period. The room 20 particularly concentrates on the densest time of this period in art. Each room is built and experienced according to the circumstances at said stated period per the concentration. This means the primary character only experiences and has accessible what was available at the time, which is another adherence to the formula stated herein, which instills, ingrains and increases the individual user's memory's capabilities of retention in such manner that can be better remembered. The cave art room 20 is circular because caves were not created with straight lines. The floor 21 appears to be rock because there was no flooring, wallpaper, or manufactured methods of architecture or decoration. The only light in the room 20 is fire 22 because 20,000+ years ago, culture, art, history relied on fire as a source of heat and light. Technology did not work; the primary character should not have access to technology that did not exist at the given period of time. The room 20 within the palace 10, which signifies cave art, has been created so that each aspect of the experience, from fire 22, to the cold temperature, fur coats 25 to be worn, to uneven hard cut circular rock walls 23, to animal skins 26, to cave etchings 27, to cave paintings (e.g. Aurochs Painting), to paintings of bulls 24 on the wall 23, be a memorable experience, one that is instilling, engraining and for efficient recollection. A fur sitting area 29 can be included.

The cave art room 20 shown in FIG. 3-4 is an example of a specific room that houses a specific number of images. The room 10 is designed in drawing, rendering, and with the intent to manifest into physical, curatorial, and thematic embodiments to continue the affectivity of the formula across multiple platforms, mediums, and applications. FIGS. 3-4 depict the third room 20 in this particular art history REALly imaginary palace 10 in its 2D and 3D perspectives and drawn to an architecturally realistic scale. In FIG. 3, a cave painting 30 is disposed on the outside of the room 20; a preferred painting is an image resembling the spotted hyena from the Chauvet caves.

7. Create a secondary Character/s: For this particular image a secondary character has been selected to act as mentor or teacher that either can guide the primary character (and in turn the individual experiencing the situation) or can follow (depending on medium, platform and experience) the main character to guarantee instilling the information in the primary character's memory (and ultimately in turn the individual experiencing the situation across all platforms and mediums). Although he/she is not placed in this view of the Figures, the character is meant to experience with the user, microscopically the information within the rooms and macroscopically the experience within the room/area/segment of the palace as a complimentary character, at all times having its influence be more of an addition to an individual's retention capabilities than a hindrance.

8. Go through Experience (Walk through, journey, travel): For this particular image the individual walks around a circular room 20. The individual is coldest when farthest from the fire 22. The individual has no luxuries except necessities and materials present at the simulated time period, and looks to survive because of his or her circumstances. This instills a character's, and in turn an individual's, remembrance of the times, culture, and particularly the art displayed in the room 20. The character is not present in this figure because the figure is a snapshot or still representation of the application of this formula contingent on one room/area/segment.

The primary character, and in turn the individual, experiencing such (regardless of the medium, platform, or language) through experiences deduces and/or is guided intrinsically towards making conclusions about periods, cultures, and people in more than just the artistic, chronological, factual, and historical lens.

In this particular case, it can be through the experience of the 2D drawing of the cave art room 20 FIG. 3 and then repeated through the 3D renderings already created and shown in FIG. 4 through multiple platforms, mediums, products, applications, and services. The room can be embodied in media and experienced through media such as, but not limited to, a traditional book, an electronic (i.e. an e-book), an audio book, an application (i.e. an app) for a computer, smartphone, or tablet, a virtual game, a co-creation social networking platform, an online community, an augmented reality experience, a curatorial gathering, a physical/thematic structure, and the like. The experiencing of such, across more than one platform and medium, fortifies and increases the affectivity of the mnemonic technique/practice/formula according to the invention.

In conclusion, a detail, action, and/or specific instance is presented in the room 20 within the palace 10 but not all the specific happenings of going through the experience, which have been developed and adhere to the formula mentioned herein, are presented in the figures that are developed for the art history concentration (i.e. a character is created around the personality, information and life of the actual person he/she is representing within the room/segment/area). Such detail, action, or specific happening may or may not be non-fictional verified fact but nonetheless not change the validity of the information, artist, or piece presented. Details, anecdotes, verified details, actions, and/or specific happening of the artist and/or his personal life (whom created said image), ultimately through the individual implementation or combination of the above two, results in the imprinting or instillation of a memorable impression in the individual experiencing this (regardless of concentration and changing per concentration if necessary) (*through multiple platforms, mediums, and languages, experiences, physical and curatorial).

FIGS. 3-4 show one particular room 20. Each REALly imaginary Palace created can have its own given number of rooms, each containing its own given number of items within the room chosen to be presented and experienced, ultimately retained and remembered. The manifestation, both in drawing, rendering, physical, thematic, and curatorial methods is created to adhere to the effectiveness of the formulaic steps that instill the mnemonic system/practice/methodology mentioned herein therefore the quantity, quality and amount of information may very without affecting the formula so long as it is done in benefit and not hindrance of the steps and its circumstances mentioned herein.

FIGS. 5-6 show a preferred embodiment of a method for creating an experience that causes a user to retain and remember information from the experience. In step 1 of the method, the owner of the method (i.e. the Mecubed formula) or a licensed user wishing to apply the invention, selects a concentration in which something is to be remembered. In step 2, the creator gathers information regarding the topic. In step 3, information about the topic is researched, read, annotated, and prioritized. In step 4, material that is presented to an individual is selected and said information is placed in a set manner. In step 5, a REALly imaginary palace is created where the experience is to be observed contingent on all above mentioned circumstances to the formula. In step 6, a primary character is created. In step 7, a secondary character (or characters) is created whose purpose is to interact and communicate with the primary character. In step 8, the individual goes through the experience.

An embodiment of the invention includes a curatorial experience. FIGS. 1-4 show an embodiment of a potential curatorial and/or thematic experience. In FIGS. 1-2, grounds of a potential physical museum (i.e. a palace 10) are shown; the museum includes rendered rooms. Various rooms are located on the potential grounds. FIGS. 3-4 show an embodiment of a room 20. The room 20 is configured to teach participants about a particular era in art history. The embodiment in FIGS. 3-4 is configured to teach about cave paintings. The room can include items like a fire 22, fur coats 24, and climatic circumstances like cold temperatures. While other rooms on the grounds are not shown in detail, the other rooms are configured, rendered and presented to teach about different eras in art history, all adhering to the invention mentioned herein.

An embodiment of the invention, which is not shown, is a book. The book is written to provide experiences as provided according to the method of the invention; In the particular case/application of the Art History concentrated palace is written with a creative storytelling lenses as a historically fictional narrative adhering to all the steps and circumstances mentioned herein.

An embodiment of the invention, which is not shown is a game, in particular, a board game. The game can be configured so that as the player(s) complete the game, they face experiences as provided by the method according to the invention.

Embodiments of the present systems and techniques, and all of the functional operations described in this specification can be implemented in digital electronic circuitry, or in computer software, firmware, or hardware, including the structures disclosed in this specification and their structural equivalents, or in physical, curatorial structures, and thematic experiences, or in combinations of them. Embodiments of the present systems and techniques can be implemented as a co-creation environment presented through a social networking technological platform, an online community, a virtual community, one or more computer program products, i.e., one or more modules of computer program instructions encoded on a computer readable medium for execution by, or to control the operation of data processing apparatus. The computer readable medium can be a machine readable device, e.g., a machine-readable storage device, storage medium, or memory device, or multiple ones thereof. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of them. This co-creation community/social networking platform is monitored and created with adherence to the formula of the mnemonic system mentioned here. A propagated signal is an artificially generated signal, e.g., a machine-generated electrical, optical, or electromagnetic signal, that is generated to encode information for transmission to suitable receiver apparatus.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment, community, social network or a combination of the aforementioned. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Information carriers suitable for storing computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the present systems and techniques can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. Examples of preferred embodiments of devices for inputting and outputting information from and to a user include books, mobile electronic devices, smartphones, personal digital assistants, tablet computers, gaming counsels, augmented reality consoles, personal computers, and the like.

Embodiments of the present systems and techniques can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the present systems and techniques, or any combination of such back-end, middleware, or front-end components. The components of the system can be interconnected by any form or medium of digital data communication, e.g., a communication network. Examples of communication networks include a local area network ("LAN"), a wide area network ("WAN") and a network of networks, e.g., the Internet.

The computing system can include clients and servers. A client and server are generally remote from each other and typically interact through a communication network. The relationship of client and server arises by virtue of computer programs running on the respective computers and having a client-server relationship to each other.

For example, the actions described in the methods can be performed in a different order and still achieve desirable results. In addition, an online analysis system (as described) can include all of the operational features described above or just a proper subset of them. The user interface functionality described can be implemented in a browser toolbar (e.g. for an internet browser such as one sold under the trade name INTERNET EXPLORER available from Microsoft of Redmond, Wash.) in which one can do direct buzz searches on a technology universe and receive browser toolbar notification of any new novel terms found in the technology universe. Multiple browsers in which the application is possibly presented is firefox, Mozilla, safari, chrome and the future browsers made to operate the internet and networks of communications via this medium. Moreover, the system can be implemented with multiple computers on a network such that different computers perform different parts of the online analysis scraping, indexing, calculation, user interaction, and presentation. Different parts of the system can be more mobile than others; for example, the user interaction or presentation could be handled by mobile phones, Personal Digital Assistants (PDAs), ipads, tablets, androids, handheld gaming systems, or other portable devices.

Another preferred embodiment of the invention is a method for co-creation of content. In the co-creation model, the method for creating a mnemonic experience is licensed to a developer. FIG. 8 outlines this implementation process applied across for example a digital platform like the internet. The owner and/or licensor of the invention creates an experience following the co-creation steps outlined above and that complies with the steps outlined in FIG. 8. The owner's of the invention and/or the licensor confirms that the experience complies with the licensed method and then approves the experience for distribution. As a result, the owner and/or licensor maintains control of the quality of media being generated by licensees. In addition, the licensor can control what experiences licensees are developing. By controlling the material being presented, the licensor can create a consistent set of experiences for various third-party observers, all of which adhere to the invention and its specific circumstances and observances. As a result, a consistent "language" of experiences is established and shared by third-party observers.

Hardware and Software

As noted above, certain aspects of the present invention may be executed by or with the help of a general purpose computer. The phrases "general purpose computer," "computer," and the like, as used herein, refer but are not limited to an engineering workstation, PC, Macintosh, PDA, web-enabled cellular phone and the like running an operating system such as OS X, Linux, Windows CE, Windows XP, Symbian OS, or the like. The phrases "General purpose computer," "computer," and the like also refer, but are not limited to, one or more processors operatively connected to one or more memory or storage units, wherein the memory or storage may contain data, algorithms, and/or program code, and the processor or processors may execute the program code and/or manipulate the program code, data, and/or algorithms. Accordingly, exemplary computer 10000 as shown in FIG. 7 includes system bus 10050 which operatively connects two processors 10051 and 10052, random access memory (RAM) 10053, read-only memory (ROM) 10055, input output (I/O) interfaces 10057 and 10058, storage interface 10059, and display interface 10061. Storage interface 10059 in turn connects to mass storage 10063. Each of I/O interfaces 10057 and 10058 may be an Ethernet, IEEE 1394, IEEE 802.11, or other interface such as is known in the art. Mass storage 10063 may be a hard drive, optical disk, or the like. Processors 10057 and 10058 may each be a commonly known processor such as an IBM or Motorola PowerPC or an Intel Pentium.

Computer 10000 as shown in this example also includes an LCD display unit 10001, a keyboard 10002 and a mouse 10003. In alternate embodiments, keyboard 10002 and/or mouse 10003 might be replaced with a pen interface. Computer 10000 may additionally include or be attached to card readers, DVD drives, or floppy disk drives whereby media containing program code may be inserted for the purpose of loading the code onto the computer.

In accordance with the present invention, computer 10000 may be programmed using a language such as Java, Objective C, C, C#, or C++, HTML5, flash, according to methods known in the art to perform the software operations described above.

In certain embodiments, although the message set order protocols and datasets described herein may be closed and proprietary, the application protocol interfaces (APIs) for interfacing with them may be published and provided as open standards.

Additional Embodiments

The invention can be embodied in any platform in which the particular product can be viewed, read, downloaded, experienced, or seen. Platforms across digital and physical mediums, including but not limited to installation, exhibition, curatorial and thematic experiences. The invention can be used with methods of communication, like website, Internet, game consoles, consoles, computers, books, textbooks, printed material, magazines, educational kits, interactive software platforms, augmented reality devices, audio version presentations, and any future technological advances to the above mentioned.

The method according to the invention can be used to create media embodied as any of the following:

Books. Any form of presented information, e.g. textbooks, books, Internet presentations, pamphlets, manifestos, e-books, images, and audiobooks.

Software Applications. Software applications for various platforms including tablet computers, smartphones, computers, mobile devices, game counsels, network appliances, and media displayers.

Games. Computer games, card games, and board games.

Audio presentation. Songs, speeches, lectures, and freestyle presentations.

Tutorials (Presented via multiple platforms including but not limited to online channels, conferences (on the educational as well as business level), or in person presentations, lectures, presentations, etc.)

Lectures. Presented across digital, physical, print and online mediums.

Websites. Any form of online, offline interaction of technology through multiple viewing platforms including but not limited to software, games, private websites and public domains.

Educational Programs. Presented as individual products/services or part of a package educational/entertainment/recreational or any established teaching method across the public or private sectors on the national, international, and worldwide level. Also includes physical, architectural structures resembling/modeling/supplementing class rooms/lecture halls/entire wings/entire school systems)

EXAMPLES OF TOPICS/SUBJECTS/CONCENTRATIONS

The method according to the invention can be applied to topics that include the following: laws, geography, science (e.g. chemistry and physics), astronomy, philosophy, medicine (e.g. gastroenterology, gynecology, brain surgery, plastic surgery), music, languages, wines, foods, history, wars, economics, stock markets, sports (e.g. golf, badminton, baseball, football, rugby, tennis, ping pong, Olympic sports, athletes, and record holders), specific years (in either a country, continents or world's events to show dimensionality both horizontal and vertically possible across concentrations), literature (across specific genre's like historical fiction, non fiction, fantasy or related to styles of writing, or years of publishing, or an individual authors' life of writing and publications, people (user's can relate to influential, powerful, eventful, forgotten, president, dictators, peace makers, CEO's, athletes, organizations, companies, and teams), nature (e.g. as large as ecosystems or as small as elements, atoms, or particular animals), anthropology, sociology, entrepreneurship, marketing, management, architecture, interior design, productions, politics, psychology, physical therapy, public relations, cars, guns, books, software applications, games (including games of chance), commodities, luxuries, technologies, artists, sales, advertising, and promotional activities.

RAMIFICATIONS AND SCOPE

Although the description above contains many specifics, these are merely provided to illustrate the invention and should not be construed as limitations of the invention's scope. Thus it will be apparent to those skilled in the art that various modifications and variations can be made in the system and processes of the present invention without departing from the spirit or scope of the invention.

What is claimed is:

1. A method for creating a mnemonic experience for a user, which comprises:
    selecting a concentration of information to be remembered;
    gathering information on said concentration, said information being intended to be remembered by the user;
    providing a building;
    placing a display to be observed in said building, said display teaching said information when observed by the user;
    providing a character to interact with the user and said display, said character being contextually related to said display;
    interacting said character with the user with while the user observes said display;
    gathering further information on said concentration;
    determining an importance of said information relative to an importance of said further information; and
    not creating a display of said further information when said importance of said further information is less than the importance of said piece of information.

2. The method according to claim 1, wherein said importance of said further information and said importance of said information are based on a probability of the user learning about said concentration by remembering said information.

3. The method according to claim 1, which further comprises:
    placing a further display to be observed in said building, said display teaching said further information when observed by the user; and
    locating said display and said further display to cause the user to remember about said concentration.

4. The method according to claim 1, wherein said concentration is art history, said display portrays an artwork, and said character portrays a person from when said artwork was created.

5. The method according to claim 1, wherein said information is the same as said display.

6. The method according to claim 1, which further comprises incorporating as many senses as possible in said display.

7. The method according to claim 1, which further comprises researching said information.

8. The method according to claim 1, which further comprises:
    providing a room within said building; and
    disposing said display in said room.

9. The method according to claim 1, wherein said building is a palace.

10. The method according to claim 1, which further comprises:
providing a further character; and
interacting said further character with said character while the user observes said display.

11. The method according to claim 10, wherein said further character is contextually related to said display.

12. The method according to claim 1, wherein said building, said display, and said character are virtual.

13. The method according to claim 12, wherein said building, said display, and said character are computer-generated.

14. The method according to claim 1, wherein
said building, said display, and said character are described in a story in a book.

15. A method for creating a mnemonic experience for a user, which comprises:
selecting a concentration of information to be remembered;
gathering information on said concentration, said information being intended to be remembered by the user;
providing a building;
placing a display to be observed in said building, said display teaching said information when observed by the user;
providing a character to interact with the user and said display, said character being contextually related to said display;
interacting said character with the user with while the user observes said display;
gathering further information on said concentration, said further information being intended to be remembered by the user;
researching said information and determining an importance of said information with respect to memorizing said information;
researching said further information and determining an importance of said information with respect to memorizing said information;
selecting at least one of said information and said further information based on said importance of said information relative to said importance of said further information;
providing a further display to be observed in said building, said further display teaching said further information when observed by the user;
placing said further display relative to said display based on said importance of said further information relative to said importance of said information;
providing a further character; and
interacting said further character with said character while the user observes said display.

16. A computer-readable medium encoded with a computer program comprising instructions that, when executed, operate to cause a computer to perform operations comprising:
selecting a concentration of information to be remembered;
gathering a piece of information on said concentration, said piece of information is to be remembered by the user;
creating a building;
placing a display to be observed in said building, said display teaching said piece of information when observed by the user;
providing a character to interact with the user and said display, said character being contextually related to said display;
interacting said character with the user with while the user observes said display;
providing a further character;
interacting said further character with said character while the user observes said display;
gathering further information on said concentration;
determining an importance of said information relative to an importance of said further information; and
not creating a display of said further information when said importance of said further information is less than the importance of said piece of information.

17. A method for co-creating a mnemonic experience, which comprises:
selecting a concentration of information to be remembered;
creating a building;
creating a room within said building, said room being assigned a sub concentration of said concentration;
providing access to said room to a licensee when a licensee agrees to a licensing agreement;
transmitting information on said sub concentration from said licensee to a licensor;
approving said information when said information complies with a rule in said licensing agreement; and
generating a display to be disposed in said room based on said information.

18. The method according to claim 17, which further comprises preventing a user from changing said information after approving said information.

19. The method according to claim 17, which further comprises:
creating a further room within said building, said further room being assigned a further sub concentration of said concentration;
providing access to said further room when a further licensee agrees to said licensing agreement;
transmitting information on said further sub concentration from said further licensee to said licensor;
approving said information when said information on said further sub concentration complies with said rule in said licensing agreement;
generating a further display to be disposed in said further room on said information on said further sub concentration;
preventing said user from changing said further display after approving said information on said further sub concentration;
approving said building after approving said first room and said second room; and
preventing said user, said licensee, or said further licensee from changing said building after approving said building.

20. A method for performing a thematic experience for creating a memory to be remembered by a user of the curatorial experience; which comprises:
selecting a location for a performance of the curatorial experience;
selecting a concentration of information to be remembered;
gathering information on said concentration;
providing a display to be observed in said location, said display teaching said piece of information when observed and experienced by the user;
providing a character to interact with the user and said display, said character being contextually related to said display;

interacting said character or representation of said character with the user and said display in said location;
providing a further character, said further character being contextually related to said display;
interacting said further character with said character and the user and the display in said location;
gathering further information on said concentration;
determining an importance of said information relative to an importance of said further information; and
not creating a display of said further information when said importance of said further information is less than the importance of said piece of information.

21. The method according to claim 20, which further comprises:
gathering further information on said concentration;
selecting a further location for a further performance;
providing a further display to be observed in said further location, said further display being intended to teach said further information when observed by the user; and
interacting said character and the user with said further display in said further location.

\* \* \* \* \*